United States Patent
Takahashi et al.

(10) Patent No.: US 7,522,287 B2
(45) Date of Patent: Apr. 21, 2009

(54) PHOTOTHERMAL CONVERSION MEASUREMENT APPARATUS, PHOTOTHERMAL CONVERSION MEASUREMENT METHOD, AND SAMPLE CELL

(75) Inventors: Eiji Takahashi, Kobe (JP); Hiroyuki Takamatsu, Kobe (JP); Masato Kannaka, Kobe (JP); Naokazu Sakoda, Kobe (JP); Tsutomu Morimoto, Kobe (JP)

(73) Assignee: Kobe Steel, Ltd., Hyogo (JP)

( * ) Notice: Subject to any disclaimer, the term of this patent is extended or adjusted under 35 U.S.C. 154(b) by 361 days.

(21) Appl. No.: 11/350,954

(22) Filed: Feb. 10, 2006

(65) Prior Publication Data

US 2006/0181708 A1 Aug. 17, 2006

(30) Foreign Application Priority Data

| Feb. 14, 2005 | (JP) | ............................. 2005-035964 |
| Mar. 1, 2005 | (JP) | ............................. 2005-056621 |
| Mar. 20, 2005 | (JP) | ............................. 2005-056249 |
| Mar. 29, 2005 | (JP) | ............................. 2005-094322 |

(51) Int. Cl.
- G01B 11/02 (2006.01)
- G01N 21/00 (2006.01)
- G01N 1/10 (2006.01)

(52) U.S. Cl. .................................................. 356/503
(58) Field of Classification Search ................. 356/432, 356/450, 451, 479, 497, 498, 503, 504

See application file for complete search history.

(56) References Cited

U.S. PATENT DOCUMENTS

| 4,938,593 | A | * | 7/1990 | Morris et al. ................. 356/344 |
| 5,298,970 | A | * | 3/1994 | Takamatsu et al. ........... 356/487 |
| 5,408,327 | A | * | 4/1995 | Geiler et al. .................. 356/432 |
| 5,619,326 | A | * | 4/1997 | Takamatsu et al. ........... 356/487 |
| 6,015,969 | A | * | 1/2000 | Nathel et al. ............ 250/227.27 |
| 7,075,058 | B2 | * | 7/2006 | Chinn et al. ................. 250/234 |
| 7,277,178 | B2 | * | 10/2007 | Shpantzer et al. ............ 356/451 |
| 7,295,325 | B2 | * | 11/2007 | Kwak et al. .................. 356/502 |

FOREIGN PATENT DOCUMENTS

| JP | 5-23072 | 6/1991 |
| JP | 10-232210 | 2/1997 |
| JP | 2000-356611 | 6/1999 |
| JP | 2004-301520 | 3/2003 |

* cited by examiner

Primary Examiner—Michael A Lyons
(74) Attorney, Agent, or Firm—Reed Smith LLP; Juan Carlos A. Marquez, Esq.

(57) ABSTRACT

A liquid sample is irradiated with excitation light and measurement light, and a measurement position at which a traveling path of the measurement light passes through an excitation section of the excitation light in the sample is changed while the sample is being irradiated with the excitation light and the measurement light. Then, the phase change of the measurement light is measured for each measurement by optical interferometry on the basis of the measurement light after the measurement light passes through the sample. The measurement position is changed by, for example, scanning the excitation light, moving the sample, moving a lens that collects the excitation light in the sample so as to change the light-collecting position (focal position) in the sample, etc.

19 Claims, 14 Drawing Sheets

FIG. 13
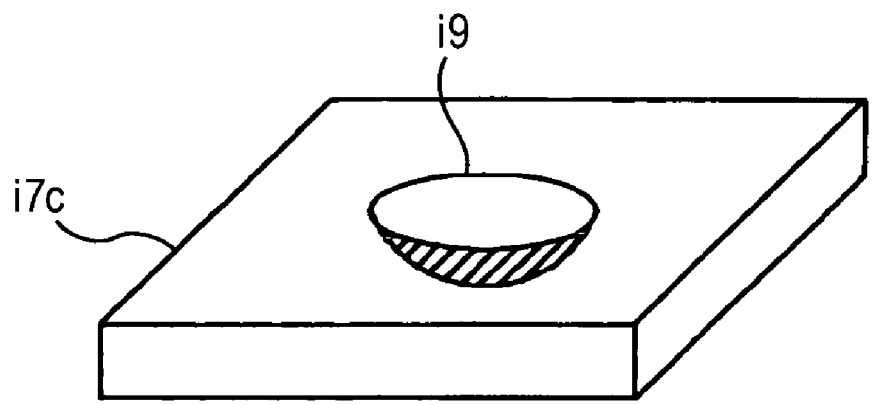
FIG. 14A    FIG. 14B
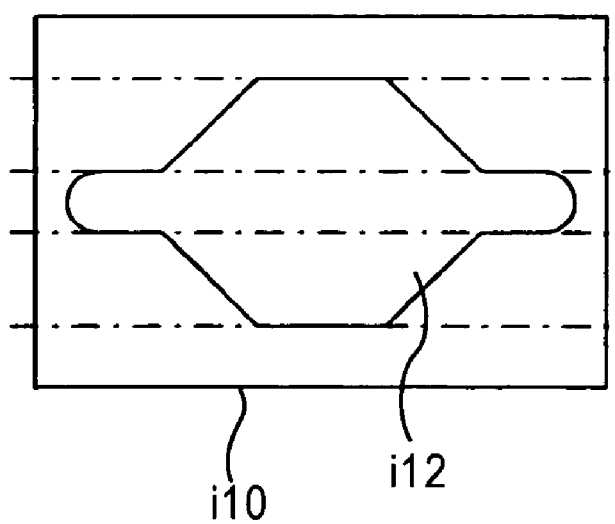
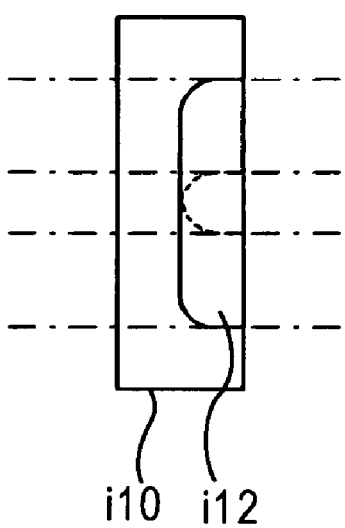

PRIOR ART

PHOTOTHERMAL CONVERSION MEASUREMENT APPARATUS, PHOTOTHERMAL CONVERSION MEASUREMENT METHOD, AND SAMPLE CELL

BACKGROUND OF THE INVENTION

1. Field of the Invention

The present invention relates to a photothermal conversion measurement apparatus and a photothermal conversion measurement method used in a process of analyzing, for example, a substance contained in a liquid sample to measure a property change of the sample based on a change in the refractive index of the sample that is caused by a photothermal effect when the sample is irradiated with excitation light. The present invention also relates to a sample cell that contains the liquid sample to be analyzed.

2. Description of the Related Art

In the analysis of substances contained in samples, such as various kinds of liquid samples, it is important to increase the analytical sensitivity in order to reduce the amounts of reagents, to simplify the process of concentrating the samples, to improve the analytical efficiency, and to reduce costs.

On the other hand, when a portion of a sample is irradiated with excitation light, the irradiated portion absorbs the excitation light and generates heat. This is called a photothermal effect, and a measurement of the thus generated heat is called a photothermal conversion measurement.

As an example of a known high-sensitivity analysis method by which a sample is analyzed using the photothermal conversion measurement, a method that uses a thermal lens effect that occurs in the sample due to the photothermal effect (hereafter called a thermal lens method) is known.

An analysis apparatus using the thermal lens method (photothermal conversion spectroscopic analysis apparatus) is disclosed in, for example, Japanese Unexamined Patent Application Publication No. 10-232210. In this apparatus, detection light (measurement light) is caused to be incident on a sample and is collected such that the detection light passes through a pinhole. The intensity of the detection light that comes out from the pinhole is detected, and accordingly a change in the refractive index of the sample caused by heat generated by the sample when excitation light is incident on the sample is detected as a change in the state in which the detection light is collected.

On the other hand, according to Japanese Unexamined Patent Application Publication No. 2004-301520, a change in the refractive index of a sample caused by a photothermal effect thereof is determined by measuring a phase change of measurement light that passes through (that is transmitted by) the sample by optical interferometry.

Accordingly, even if the position of a photodetector (photoelectric conversion means), the intensity of the measurement light, and the intensity distribution of the measurement light differ for each apparatus, a change in the refractive index of the sample can be stably measured with high optical accuracy and sensitivity without being influenced by such factors as long as they do not vary during the measurement. This solves the problems of the above-described thermal lens method.

On the other hand, Japanese Unexamined Utility Model Registration Application Publication No. 5-23072 discloses a technique for measuring a spectrum of a Fourier interference pattern obtained by a Fourier spectrometer with a high dynamic range.

In addition, Japanese Unexamined Patent Application Publication No. 2000-356611 discloses a high-sensitivity analysis method using the photothermal conversion measurement as an in-situ analysis technique that meets the needs for high-speed, high-sensitivity detection of small amounts of biomolecules in a microchannel. The analysis using the photothermal conversion measurement is known to be effective in detecting, for example, a small amount of molecules after a measured substance is separated by chromatography, and various improvements have been suggested to increase the analysis speed and sensitivity.

FIG. 17 is a schematic diagram illustrating a photothermal conversion measurement apparatus jXO as an example of a known photothermal conversion measurement apparatus. The photothermal conversion measurement apparatus jXO will be explained below with reference to FIG. 17.

As shown in FIG. 17, the photothermal conversion measurement apparatus jXO includes an excitation light source j1, a chopper j2, a dichroic mirror j3, a lens j4, a measurement light source j6, a half-wave plate j7, a mirror j22, a polarizing beam splitter (PBS) j8, acousto-optical modulators j9 and j10, mirrors j11 and j12, polarizing beam splitters (PBS) j13 and j14, a mirror j15, quarter-wave plates j16 and j18, a photodetector j17, a reflection mirror j19, a polarizing plate j20, and a signal processor j21. A sample cell j5 containing a sample to be analyzed is disposed at a predetermined position. The sample cell j5 contains the sample to be analyzed, and is filled with, for example, a sample dissolved in a solvent. In the following description, if a solvent is contained in the sample cell, it is to be considered that the solvent is included in the sample cell.

The excitation light source j1 emits excitation light E. The excitation light source j1 is, for example, a laser with a wavelength of 533 nm and an output of 100 mW (yttrium aluminum garnet (YAG) harmonic wave). The excitation light E is converted into chopped light by a predetermined period by the chopper j2. Then, the excitation light E is reflected by the dichroic mirror j3, passes through the lens j4, and is incident on the sample contained in sample cell j5. The sample contained in the sample cell j5 absorbs the excitation light E and generates heat (photothermal effect), and the thus generated heat is absorbed by the solvent. Accordingly, the refractive index of the sample changes.

Measurement light M for measuring the change in the refractive index of the sample is emitted by the measurement light source j6. The measurement light source j6 is, for example, a He—Ne laser with an output of 1 mW. The measurement light M enters the half-wave plate j7, where the plane of polarization of the measurement light M is adjusted, and is reflected by the mirror j22. Then, the measurement light M is divided by the PBS j8 into two polarized waves M1 and M2 that are perpendicular to each other.

The polarized waves M1 and M2 enter the acousto-optical modulators j9 and j10, respectively, and are frequency-converted. At this time, the frequencies of the polarized waves M1 and M2 are set so as to differ from each other by, for example, 30 MHz. Then, the polarized waves M1 and M2 are reflected by the mirrors j11 and j12, respectively, and are combined by the PBS j13.

The polarized wave M2 in the combined wave passes through (is transmitted by) the PBS j14, is reflected by the mirror j15, and enters the PBS j14 again. Since the polarized wave M2 passes through the quarter-wave plate j16 disposed between the PBS j14 and the mirror j15 twice, the plane of polarization thereof is rotated by 90°. The polarized wave M2 is reflected by the PBS j14 toward the photodetector j17.

The polarized wave M1 in the combined wave is reflected by the PBS j14, passes through the quarter-wave plate j18, the dichroic mirror j3, and the lens j4, and is incident on the sample in the sample cell j5. In this apparatus, the polarized wave M1 and the excitation light are incident on the sample at the same irradiation position in the sample cell j5.

The polarized wave M1 passes through the sample cell j5, is reflected by the reflection mirror j19, and returns to the PBS j14 along the same optical path as the optical path along which the polarized wave M1 travels to the sample cell. Since the polarized wave M1 passes through the quarter-wave plate j18 twice, the plane of polarization thereof is rotated by 90°. Accordingly, the polarized wave M1 is combined with the polarized wave M2 when the polarized wave M1 passes through the PBS j14 and the combined light travels toward the photodetector j17.

The polarizing plate j20 is disposed between the PBS j14 and the photodetector j17. In the polarizing plate j20, the polarized wave M1 and the polarized wave M2 interfere with each other as measurement light and reference light, respectively.

The photodetector j17 detects the interference light obtained by the polarized waves M1 and M2 and outputs an electric signal representing the intensity of the interference light to the signal processor j21.

The intensity of the interference light varies depending on a phase change when the polarized wave M1, which functions as the measurement light, passes through the sample cell j5. Accordingly, the phase change of the polarized wave M1, which functions as the measurement light, can be determined on the basis of the measurement result of the intensity of the interference light. Thus, a change in the refractive index of the solvent filling the sample cell j5 can be determined.

In each of the structures described in Japanese Unexamined Patent Application Publication Nos. 10-232210 and 2004-301520, substantially the entire path along which the measurement light travels in the sample is excited by the excitation light and an average property of the entire path of the measurement light in the sample is measured. Therefore, a property distribution in the sample, in particular, a property distribution along the depth of the sample from the surface thereof cannot be obtained.

When the absorption spectral property of the sample is to be evaluated, a white light source is used as the excitation light source. White light emitted from the white light source is divided into spectral components and the measurement is performed each time the wavelength range of the excitation light is changed. A typical white light source generally has a wide light-emitting section, and therefore it is difficult to collect light emitted from the white light source with high accuracy before irradiating the sample with the light.

However, the white light source cannot be used in the measurement using the thermal lens method described in Japanese Unexamined Patent Application Publication No. 10-232210, since the excitation light must be collected with high accuracy before irradiating the sample therewith in order to obtain the thermal lens effect. Therefore, a laser oscillator with a specified wavelength range must be used and it is difficult to evaluate the absorption spectral property of the sample. Although the absorption spectral property of the sample can, of course, be evaluated by the thermal lens method if a plurality of laser oscillators with different wavelength ranges or a laser oscillator with a variable wavelength range is used, the structure of the apparatus becomes complex and the cost is increased in such a case.

In addition, in the measurement using the thermal lens method described in Japanese Unexamined Patent Application Publication No. 10-232210, the intensity of the excitation light must be increased or the diameter of the pinhole through which the measurement light travels after passing through the sample must be reduced in order to increase the measurement sensitivity. However, if the intensity of the excitation light is increased, electric power consumption and cost are also increased. In addition, if the pinhole diameter is reduced, a signal-to-noise (S/N) ratio is reduced due to a reduction in the amount of light received by the photodetector and the measurement time is increased.

In addition, in the measurement described in Japanese Unexamined Patent Application Publication No. 2004-301520, since an optical interferometer, in which a relatively large number of optical devices must be arranged with high positioning accuracy, is used, the structure of the apparatus is complex. In addition, although the optical interferometer is largely influenced by disturbance noise, such as vibration, it is difficult to reduce the disturbance noise.

The accuracy of the analysis depends on the intensity of a detection signal that varies in accordance with the temperature change of the solvent. Therefore, it is desirable to obtain a high-intensity detection signal to increase the analysis accuracy.

To obtain a high-intensity detection signal, it is necessary to cause the sample to generate a large amount of heat. In other words, it is necessary to set the intensity of the excitation light incident on the sample as high as possible. However, if a high-intensity (high-brightness) light source is used as the excitation light source, electric power consumption and cost are increased.

When the sample contained in the sample cell is measured, members other than the sample, such as a container member of the sample cell and the solvent enclosed therein, are also irradiated with the excitation light E emitted from the excitation light source j1. Therefore, if the wavelength range of the excitation light includes the absorption wavelength range of the container member or the solvent, a part of the excitation light is absorbed by the container member or the solvent, and accordingly the container member or the solvent generates heat.

FIGS. 18A to 18C are graphs showing examples of optical absorption properties of a measurement sample, a container member, and a solvent, respectively. In each graph, the horizontal axis shows the frequency of light (reciprocal of the wavelength of light) and the vertical axis shows the optical absorptivity. The sample is linseed oil and the solvent is chloroform.

As shown in FIG. 18A, the optical absorptivity of the sample (linseed oil) has peaks in frequency ranges of 1400 $cm^{-1}$ to 1470 $cm^{-1}$ and 1710 $cm^{-1}$ to 1770 $cm^{-1}$.

As shown in FIG. 18B, the container member efficiently absorbs light with a frequency range of 1100 $cm^{-1}$ or less. Therefore, if the excitation light has a component with a frequency of 1100 $cm^{-1}$ or less, the container member absorbs a part of the excitation light and generates heat.

In addition, as shown in FIG. 18C, light that is easily absorbed by the solvent (chloroform) has a frequency range of 1400 $cm^{-1}$ to 1550 $cm^{-1}$. Therefore, the solvent generates heat if the excitation light has a component with a frequency in the range of 1400 $cm^{-1}$ to 1550 $cm^{-1}$.

When the solvent of the sample or the container member generates heat as described above, the signal input to the signal processor j21 includes a noise signal generated due to heat generated by the members other than the sample. Thus, the heat generated by the members other than the sample causes a reduction in the measurement accuracy of the heat generated by the sample.

Accordingly, frequency components of the excitation light other than those with frequency ranges (wavelength ranges) that can be easily absorbed by the sample are preferably eliminated before the excitation light is incident on the sample. More specifically, in the example shown in FIGS. 18A to 18C, components with frequency ranges of 1100 cm$^{-1}$ or less and 1470 cm$^{-1}$ to 1550 cm$^{-1}$ are preferably eliminated.

SUMMARY OF THE INVENTION

In view of the above-described situation, the present invention provides a photothermal conversion measurement apparatus, a photothermal conversion measurement method, and a sample cell that produces the following effects.

That is, distribution of property change caused by the photothermal effect in a sample can be easily measured.

In addition, the measurement of the property change caused by the photothermal effect in the sample including the measurement of the absorption spectral property of the sample can be performed with high sensitivity using a simple structure, and the influence of disturbance noise, such as vibration, can be reduced.

In addition, high-accuracy measurement can be performed by increasing the intensity of the excitation light incident on the sample using a simple structure and with low cost.

In addition, high-accuracy sample analysis can be achieved by reducing heat generated by a container member that contains the sample and a solvent enclosed therein.

In order to achieve the above-described objects, the present invention provides a photothermal conversion measurement apparatus and a photothermal conversion measurement method for measuring a property change of a sample caused by a photothermal effect of the sample when the sample is irradiated with excitation light, wherein a measurement-light-emitting unit irradiates the sample with predetermined measurement light, a measurement-position-changing unit changes a measurement position at which a traveling path of the measurement light passes through an excitation section of the excitation light in the sample, and the property change of the sample is measured for each measurement position on the basis of the measurement light after the measurement light passes through the sample.

The property change of the sample is preferably measured on the basis of the measurement light by measuring a phase change of the measurement light that passes through the sample by optical interferometry, as described in Japanese Unexamined Patent Application Publication No. 10-232210. Alternatively, the property change may also be measured by a thermal lens method, as described in Japanese Unexamined Patent Application Publication No. 2004-301520.

Since the measurement can be performed while changing the measurement position (position where the path of the measurement light passes through the excitation section) in the sample, distribution of the property change caused by the photothermal effect of the sample can be measured. In particular, a change in the refractive index of the sample caused by the photothermal effect thereof can be measured on the basis of the phase change of the measurement light that passes through (is transmitted by) the sample by optical interferometry. In such a case, even if, for example, the arrangement of devices, the intensity of the measurement light, etc., differ for each apparatus, the change in the refractive index (property change) of the liquid sample can be measured with high repeatability (stability), accuracy, and sensitivity without being influenced by such factors as long as they to not vary during the measurement.

The measurement position may be changed by, for example, changing the optical path of the excitation light (optical-path changing unit), moving the position of the sample (sample-moving unit) or a combination thereof. Accordingly, it is not necessary to move a device relating to the measurement light (device for measuring the phase change of the measurement light by optical interferometry) that has a large number of components, and therefore the structure of the apparatus is simple.

More specifically, the optical path of the excitation light may be changed by changing an incident position and/or an incident direction of the excitation light that is incident on the sample in a direction that intersects an incident direction of the measurement light on the sample (first optical-path changing unit). Alternatively, the optical path of the excitation light may also be changed by moving a lens, which allows the excitation light to pass therethrough in substantially the same direction as the incident direction of the measurement light on the sample while collecting the excitation light, in substantially the same direction as the incident direction of the measurement light to change a focus position (light-collecting position) of the excitation light in the sample (second optical-path changing unit).

In the former case (first optical-path changing unit), a portion where the measurement light and the excitation light intersect in the sample (measurement position) is changed. In the latter case (second optical-path changing unit), only the focal position (light-collecting position) of the excitation light in the sample, which changes as the lens is moved, serves as the main excitation section, and the excitation section (measurement position) is moved along the path of the measurement light.

In the former case, the optical path of the excitation light can be changed using a simple structure in which, for example, a deflection mirror for deflecting the excitation light is slightly moved. However, in this case, if the irradiation area of the sample is small, there is a risk that the incident position at which the excitation light is incident on the sample in a direction that intersects the measurement light cannot be set within the irradiation area.

In comparison, in the latter case, the measurement light and the excitation light are incident on the sample along substantially the same axis. Therefore, the measurement position can be changed even if the irradiation area of the sample is small.

In addition, to measure the property change of the sample caused by the photothermal effect of the sample when the sample is irradiated with the excitation light on the basis of the measurement light that passes through the sample, the following structures may be used.

That is, two light-reflecting units that reflect light incident thereon may be arranged so as to face each other across the sample, at least one of the two light-reflecting units allowing a part of the incident light to pass therethrough. The two light-reflecting units repeatedly reflect the measurement light incident on the sample between the two light-reflecting units along one axis while allowing the measurement light to pass through the sample. In addition, a light-intensity detector receives the measurement light that passes through the light-reflecting unit that allows a part of the incident light to pass therethrough in a direction away from the sample and detects the intensity of the received measurement light.

The property change of the sample caused by the photothermal effect thereof is measured on the basis of the result of detection of the intensity of the measurement light that is obtained each time the state in which the sample is irradiated with the excitation light is changed.

The measurement light that reaches the light-intensity detector is a superposition of measurement-light components that travel between the two light-reflecting units, such as high-reflection mirrors, different numbers of times. When the optical path length of the measurement light between the mirrors is changed by the photothermal effect (change in the refractive index) of the sample, a larger phase shift occurs as the number of times of reflection between the mirrors is increased. Therefore, even a small change in the refractive index (optical path length) causes a large change in the detection signal from the light-intensity detector (light-intensity detection signal). As a result, the property change (change in the refractive index) caused by the photothermal effect of the sample can be measured with a higher sensitivity compared to the cases in which the above-described thermal lens method and optical interferometry are used. In addition, such a high-sensitivity measurement can be performed with a simple structure including two light-reflecting units, such as high-reflection mirrors, arranged so as to face each other and the light-intensity detector.

The fact that the change in the light-intensity detection signal is large relative to the change in the optical path length of the measurement light means that the influence of disturbance noise, such as vibration, is also large. On the other hand, the light-intensity detection signal is not supposed to vary once the excitation state of the sample becomes stable.

Accordingly, a distance-adjusting unit may be provided to adjust a distance between the two light-reflecting units such that variation in the detection signal obtained by the light-intensity-detecting unit is reduced. In such a case, the property change of the sample can be measured with high accuracy without being largely influenced by the disturbance noise, such as vibration.

In addition, an intensity modulator for periodically modulating the intensity of the excitation light incident on the sample and a periodic-component extractor that extracts a periodic component with the same period as the intensity modulation period of the excitation light from the detection signal obtained by the light-intensity detector may also be provided.

In such a case, the refractive index of the sample varies with the same period as the intensity modulation period of the excitation light. Therefore, it becomes possible to measure only the change in the refractive index of the sample while eliminating the influence of noise that does not have the frequency component of the excitation light. As a result, the S/N ratio of the measurement can be increased.

In addition, a variable spectroscopic unit that outputs light obtained by dividing white light into spectral components as the excitation light and that is capable of varying the wavelength range of the excitation light may also be provided. In such a case, the absorption spectral property of the sample may also be obtained by detecting the measurement light with the light-intensity detector each time the wavelength range of the excitation light is changed by the variable spectroscopic unit.

In the above-described photothermal conversion measurement apparatus, the excitation light for causing the photothermal effect in the sample may be deflected after the excitation light passes through the sample so that the excitation light is redirected to the sample.

In this case, since the excitation light is redirected to the sample after the excitation light passes through the sample, the sample can be efficiently irradiated with the excitation light having a certain intensity and a large amount of heat is generated by the sample. Accordingly, the analysis accuracy of the sample is increased.

If the excitation light is redirected such that the excitation light is incident on the sample at the same portion as the portion at which the excitation light is incident on the sample the first time, a certain portion of the sample effectively generates heat. Alternatively, if a large area of the sample is to be irradiated, the excitation light may be incident on the sample at a portion different from the portion at which the excitation light is incident on the sample the first time.

In addition, the excitation light is preferably collected before being incident on the sample when a small region of the sample is to be analyzed. In such a case, the region of the sample to be analyzed can be irradiated with high-density excitation light.

The excitation light may be collected using, for example, a lens or a concave mirror.

When a concave mirror is used to collect the excitation light, a concave mirror provided to deflect the excitation light as described above may be used also for collecting the excitation light.

In addition, a sample cell that contains the sample may have a structure for deflecting the excitation light. More specifically, the sample cell may have a container section that contains the sample and a reflective surface provided on a side of the container section opposite to an incident side at which the excitation light is incident on the container section, the reflective surface reflecting the excitation light after the excitation light passes through the container section.

The reflective surface may have a concave mirror that collects the excitation light. In addition, the sample cell may also have a lens for collecting the excitation light on the incident side of the container section.

As described above, if a solvent for dissolving the sample is contained in the sample cell, it is to be considered that the solvent is included in the sample cell.

When the sample to be measured is contained in a predetermined sample cell (container member), the photothermal conversion measurement apparatus may also include a filter unit that reduces or eliminates a component with a main light-absorption wavelength range of the sample cell from the excitation light. After the above-mentioned component is reduced or eliminated by the filter unit, the sample with is irradiated the excitation light to measure the property change (for example, the phase change of the measurement light incident on the sample cell). In addition, the photothermal conversion measurement apparatus may also include a filter unit that reduces or eliminates a component with a main light-absorption wavelength range of an enclosing agent (solvent or the like) enclosed in the sample cell together with the sample before the sample is irradiated with the excitation light to measure the property change.

Accordingly, members other than the sample included in the sample cell are prevented from absorbing the excitation light, and therefore the measurement accuracy of the property change of the sample is increased. The filter unit preferably has a sufficient thickness in the incident direction of the excitation light so that the component of the absorption wavelength range can be sufficiently reduced or eliminated. The filter unit may include, for example, a wavelength-selecting filter like a bandpass filter and a sharp-cut filter.

The filter unit may include a member made of the same material as the material of the sample cell or the enclosing agent. Typically, the filter unit includes an additional sample cell (with a sufficient thickness) in which the sample is not contained. In such a case, the component with the light absorption wavelength range of the sample cell can be reliably reduced or eliminated by the filter unit. It is not necessary to use a member that is exactly identical to the sample cell as long as the member is made of a material that is similar to the material of the sample cell and has an absorption wavelength range including the main absorption wavelength range of the sample cell.

In addition, the filter unit may include an enclosing-agent container that contains an enclosing agent identical to that enclosed in the sample cell together with the sample (for example, a solvent of the sample). In this case, not only the component with the absorption wavelength range of the container member in the sample cell but also the component with the absorption wavelength range of the enclosing agent enclosed in the container member may be reduced or eliminated from the excitation light. The above-described additional sample cell may be used as the enclosing-agent container. More specifically, the filter unit may include the above-mentioned additional sample cell that is filled with the enclosing agent.

When, for example, a xenon arc lamp is used as an excitation light source and a sample cell made of glass is filled with aqueous solution of a coloring material that absorbs visible light region, the glass absorbs the ultraviolet light component of the excitation light and water absorbs the infrared light component of the excitation light. In this case, a glass container filled with water is as the filter unit.

The above-described structures may be considered as a photothermal conversion measurement method using the filter unit according to embodiments of the present invention.

According to the present invention, a sample is irradiated with excitation light and measurement light, and a measurement position at which a traveling path of the measurement light passes through an excitation section of the excitation light in the sample is changed while the sample is being irradiated with the excitation light and the measurement light. Since the property change of the sample is measured for each measurement position on the basis of the measurement light after the measurement light passes through the sample, distribution of the property change caused by the photothermal effect of the sample can be measured. In particular, when the phase change of the measurement light is measured by optical interferometry (relative optical method), the property change of the liquid sample can be measured with high repeatability (stability), accuracy, and sensitivity.

When the measurement position is changed by changing an incident position and/or an incident direction of the excitation light that is incident on the sample in a direction that intersects the incident direction of the measurement light, the measurement position may be changed with a simple structure.

Alternatively, a lens that allows the excitation light to pass therethrough in substantially the same direction as the incident direction of the measurement light on the sample while collecting the excitation light may be provided, and the focus position of the excitation light in the sample may be changed by moving the lens in substantially the same direction as the incident direction of the measurement light. In this case, the measurement position can be changed even when the irradiation area of the sample is small.

In addition, two light-reflecting units may be arranged so as to face each other across the sample to repeatedly reflect the measurement light incident on the sample between the two light-reflecting units along one axis while allowing the measurement light to pass through the sample and the intensity of measurement light that passes through at least one of the two light-reflecting units may be detected. In this case, the following effects can be obtained.

That is, even a small change in the refractive index of the sample causes a large change in the light-intensity detection signal, and therefore the property change (change in the refractive index) caused by the photothermal effect of the sample can be measured with high accuracy and sensitivity. Furthermore, such a high-sensitivity measurement can be performed with a simple structure.

In addition, when a distance-adjusting unit that adjusts a distance between the two light-reflecting units such that variation in the light-intensity detection signal is reduced is provided, the property change of the sample can be measured with high accuracy while reducing the influence of disturbance noise, such as vibration.

In addition, when the intensity of the excitation light incident on the sample is periodically modulated and a component with the same period as the intensity modulation period of the excitation light is extracted from the light-intensity detection signal, the S/N ratio of the measurement can be increased.

In addition, when light obtained by dividing white light into spectral components is output as the excitation light in such a manner that the wavelength range of the excitation light can be varied and the measurement light is detected each time the wavelength range of the excitation light is changed, the absorption spectral property of the sample can be easily measured.

In addition, when the excitation light is deflected such that the excitation light is redirected to the sample, the intensity of the excitation light incident on the sample can be increased by a simple method and with low cost without using a high-intensity light source. Accordingly, the analysis accuracy of the photothermal conversion measurement can be increased.

In addition, a filter unit may be provided to reduce or eliminate a component with a wavelength range of light absorbed by the sample cell or the enclosing agent (solvent or the like) enclosed in the sample cell from the excitation light incident on the sample contained in the sample cell. In such a case, members other than the sample are prevented from generating heat, and therefore the measurement accuracy of the property change of the sample is increased.

BRIEF DESCRIPTION OF THE DRAWINGS

FIG. 13 is a perspective view of a reflective mirror included in the sample cell shown in FIG. 12;

FIGS. 14A and 14B are a front view and a side view, respectively, of a channel substrate included in the sample cell shown in FIG. 12;

DESCRIPTION OF THE PREFERRED EMBODIMENTS

Embodiments of the present invention will be described below with reference to the accompanying drawings in order to facilitate understanding of the present invention. The following embodiments are simply examples to which the present invention is applied and are not intended to limit the technical scope of the present invention.

Figure 1:
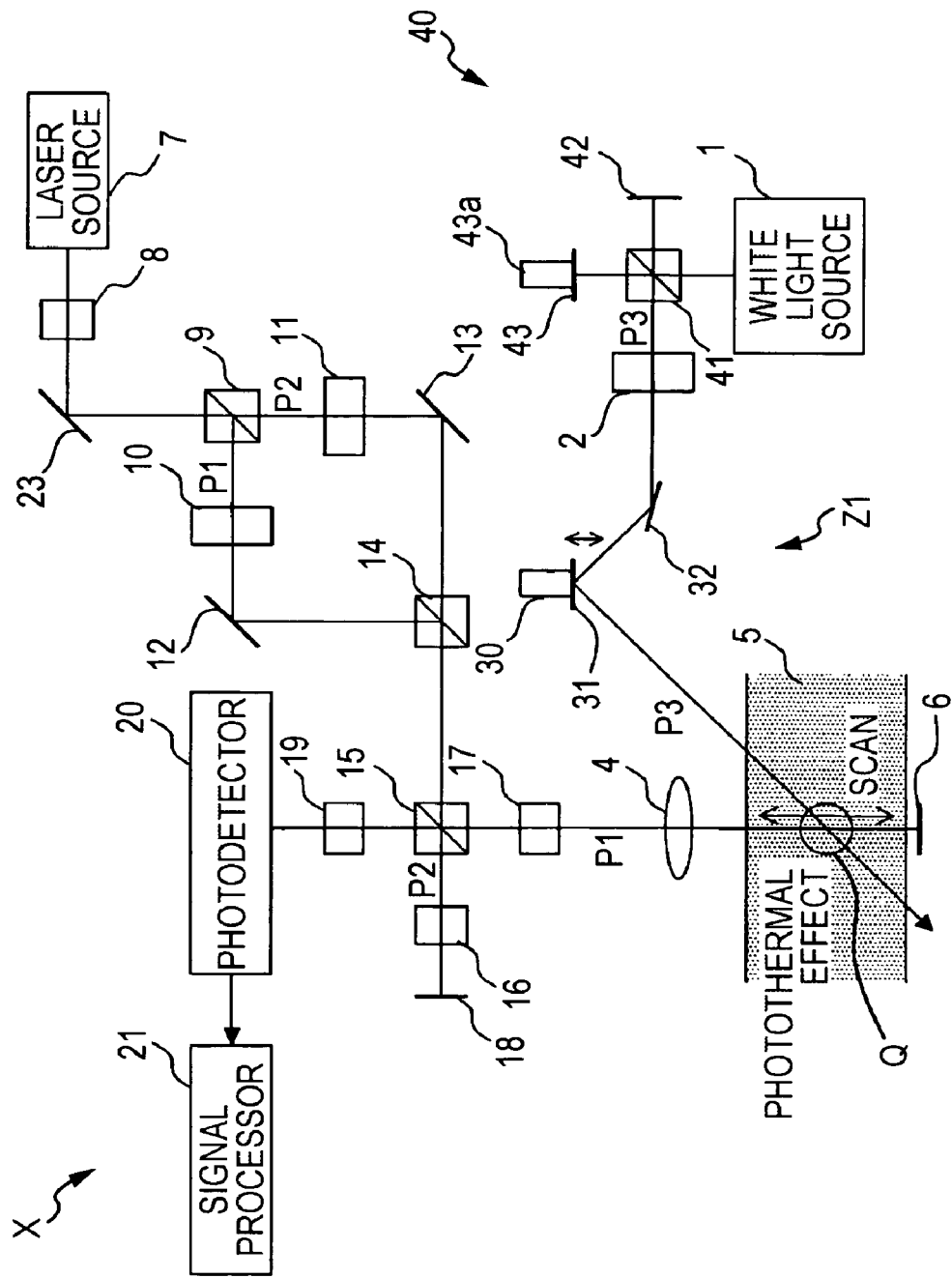
FIG. 1 is a schematic diagram of a photothermal conversion measurement apparatus according to a first embodiment of the present invention.
Figure 2:
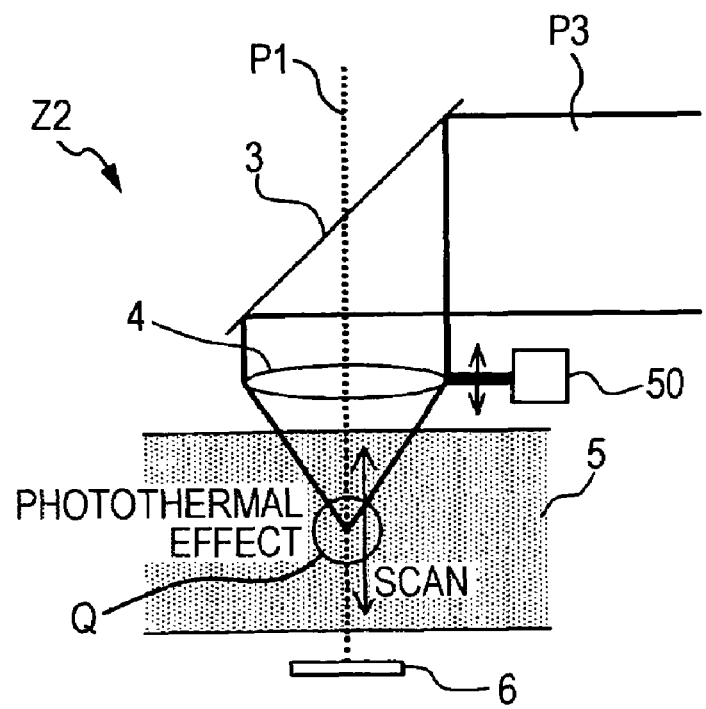
FIG. 2 is a schematic diagram of a measurement-position-scanning mechanism included in a photothermal conversion measurement apparatus according to a second embodiment of the present invention.
Figure 3:
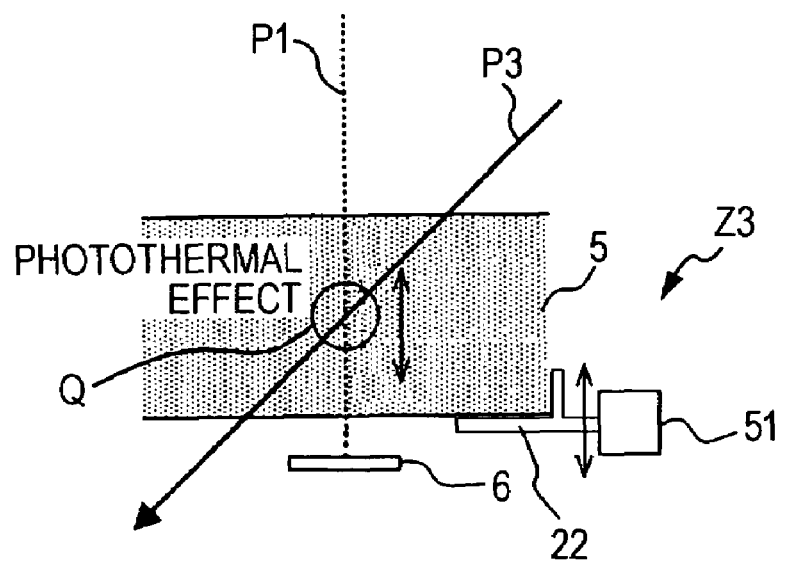
FIG. 3 is a schematic diagram of a measurement-position-scanning mechanism included in a photothermal conversion measurement apparatus according to a third embodiment of the present invention.
Figure 4:
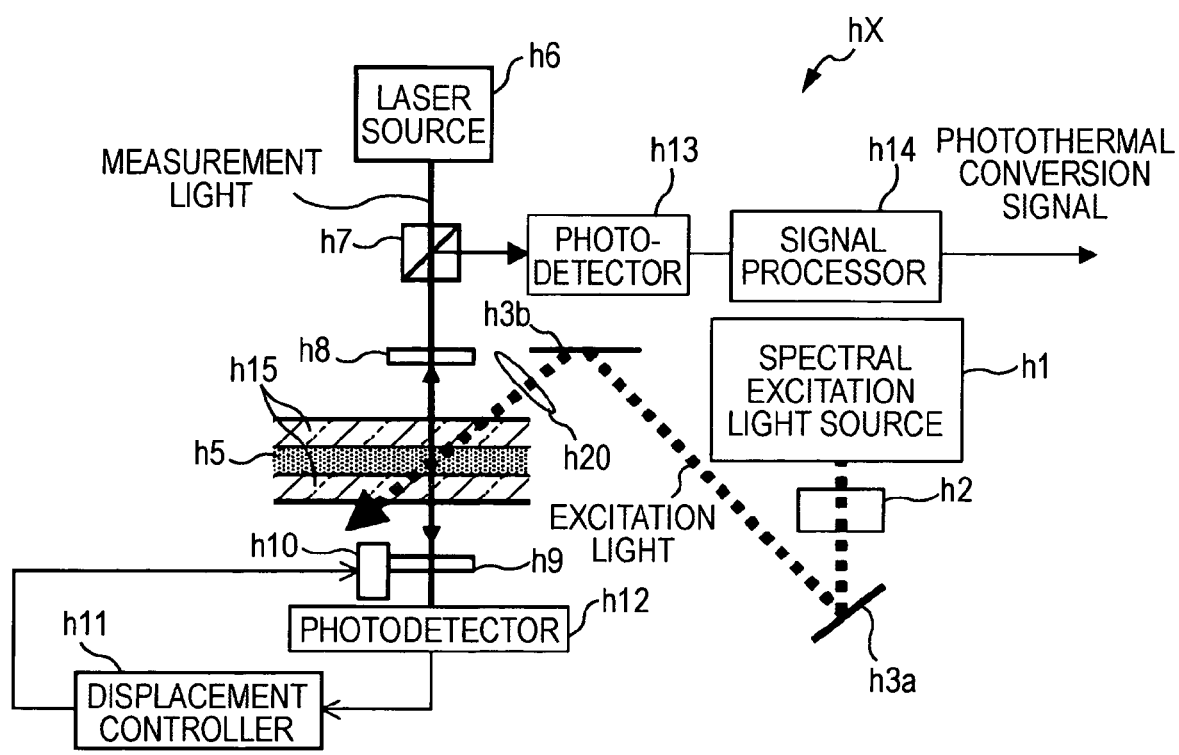
FIG. 4 is a schematic diagram of a photothermal conversion measurement apparatus according to a fourth embodiment of the present invention.
Figure 5:
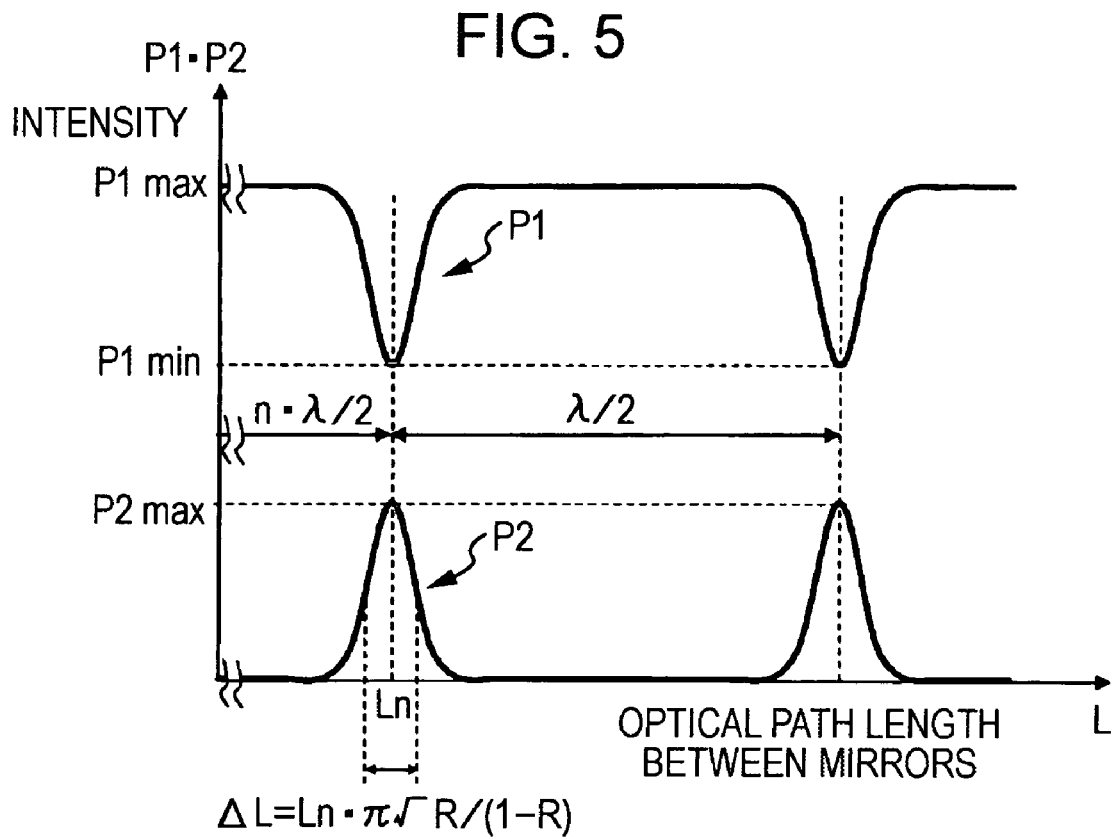
FIG. 5 is a diagram showing the relationship between the optical path length of measurement light that travels between two high-reflection mirrors in the photothermal conversion measurement apparatus according to the fourth embodiment and the intensity of the measurement light reflected or transmitted by the high-reflection mirrors.
Figure 6:
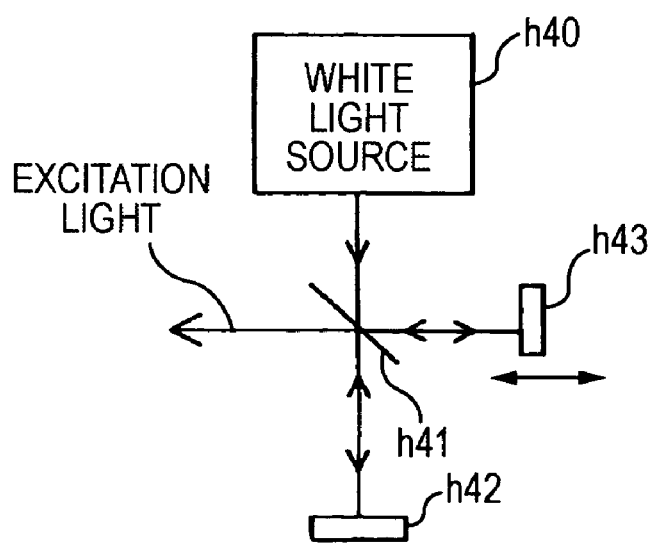
FIG. 6 is a schematic diagram of an excitation-light output unit using Fourier spectrum that can be used in the photothermal conversion measurement apparatus according to the fourth embodiment.
Figure 7:
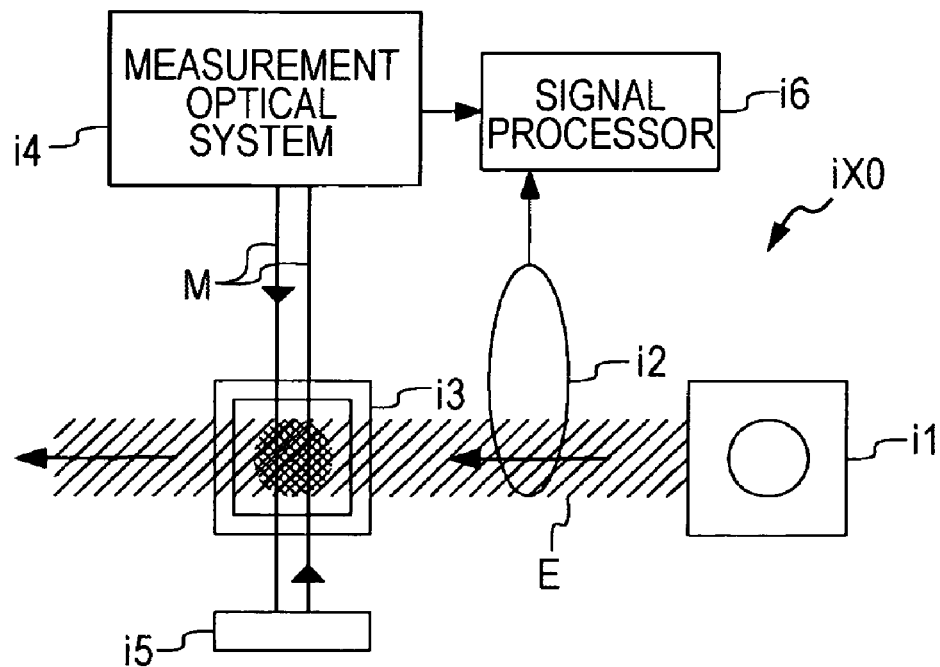
FIG. 7 is a schematic diagram illustrating an example of a known photothermal conversion measurement apparatus.
Figure 8:
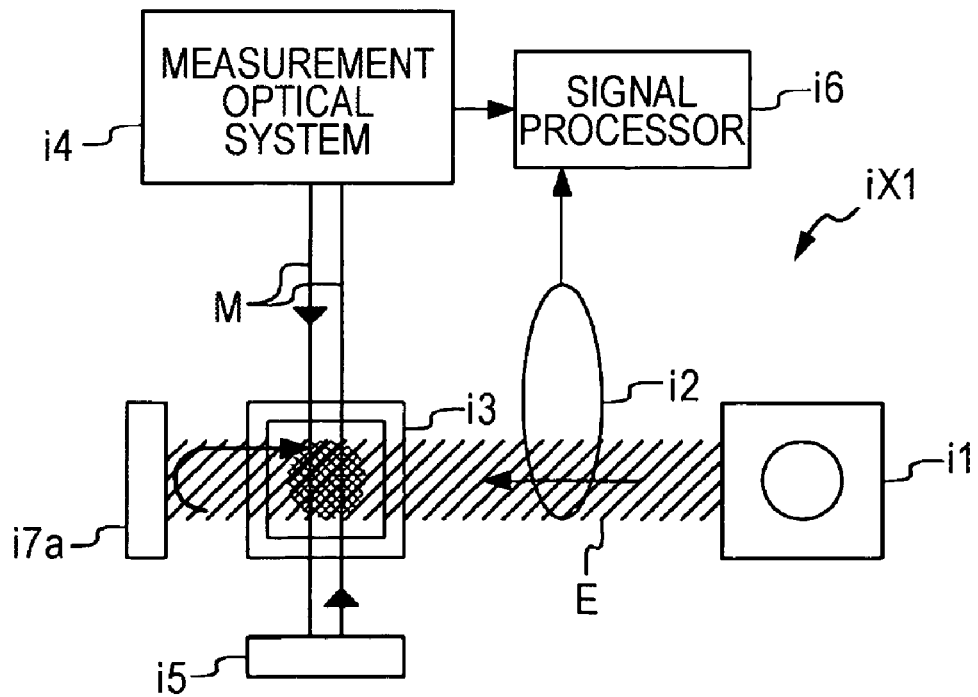
FIG. 8 is a schematic diagram illustrating a characteristic portion of a photothermal conversion measurement apparatus according to a fifth embodiment of the present invention.
Figure 9:
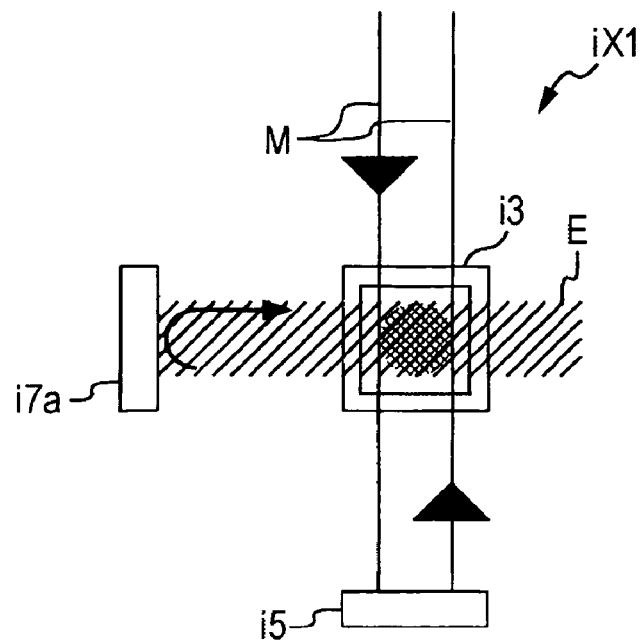
FIG. 9 is another schematic diagram illustrating the characteristic portion of the photothermal conversion measurement apparatus according to the fifth embodiment.
Figure 10:
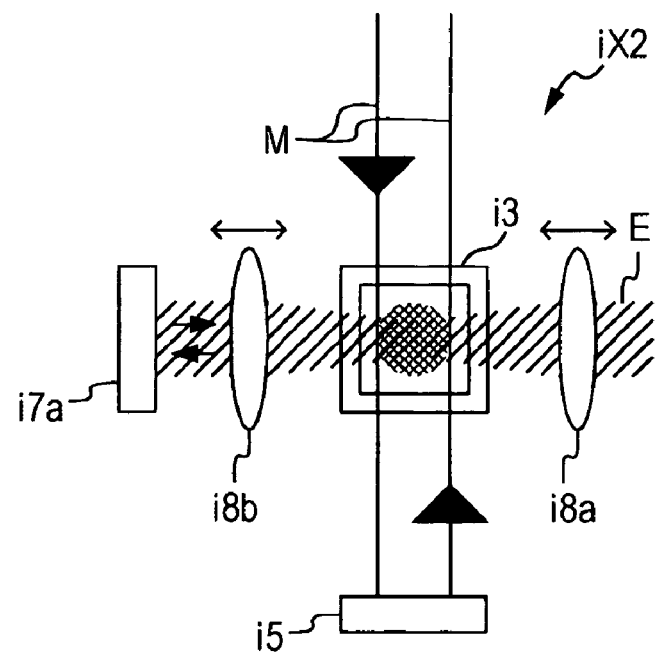
FIG. 10 is a schematic diagram illustrating a characteristic portion of a photothermal conversion measurement apparatus according to a sixth embodiment of the present invention.
Figure 11:
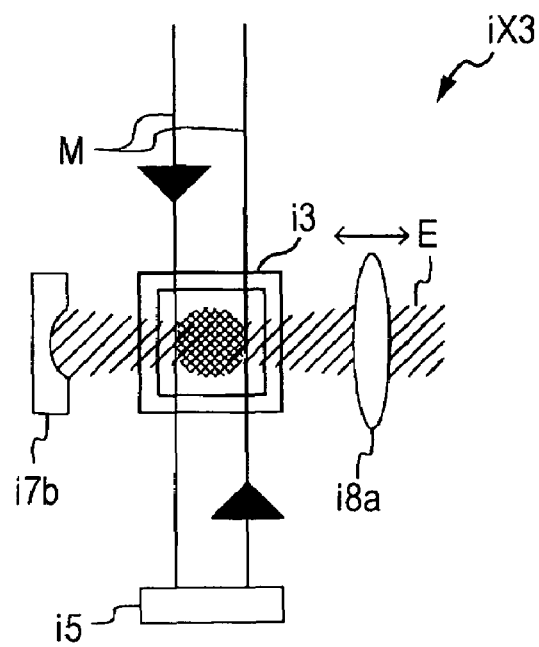
FIG. 11 is a schematic diagram illustrating a characteristic portion of a photothermal conversion measurement apparatus according to a seventh embodiment of the present invention.
Figure 12:
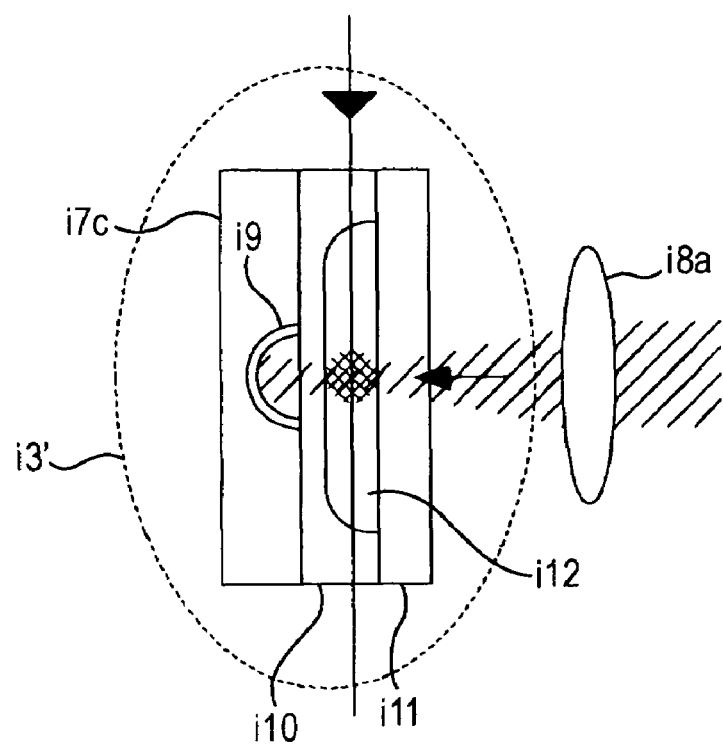
FIG. 12 is a schematic diagram illustrating a sample cell according to an embodiment of the present invention.
Figures 15A, 15B:
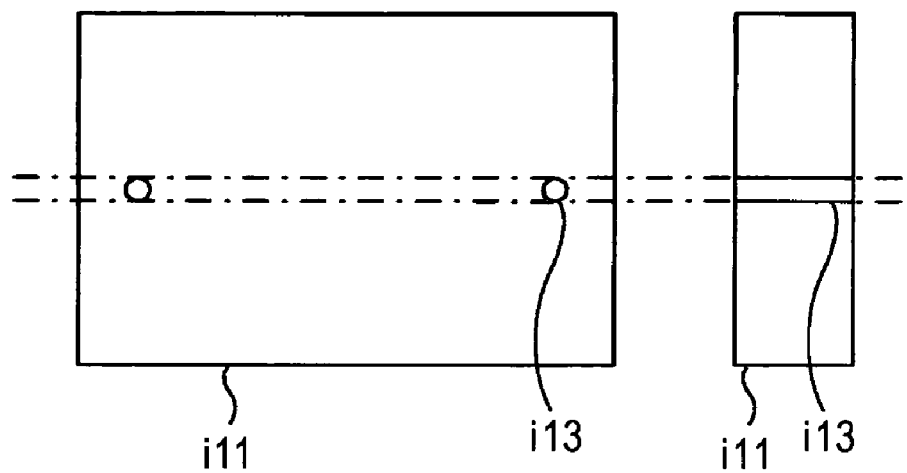
FIGS. 15A and 15B are a front view and a side view, respectively, of a cover substrate included in the sample cell shown in FIG. 12.
Figure 16:
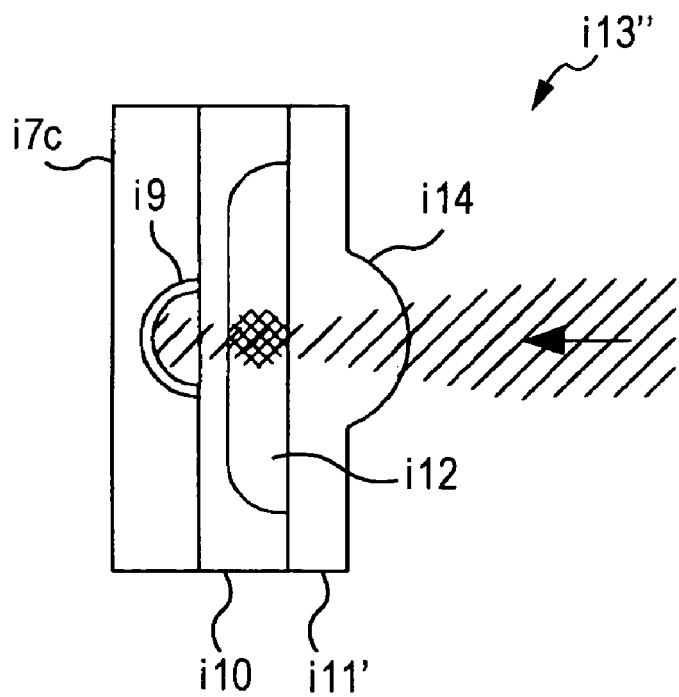
FIG. 16 is a schematic diagram illustrating a sample cell according to another embodiment of the present invention.
Figure 17:
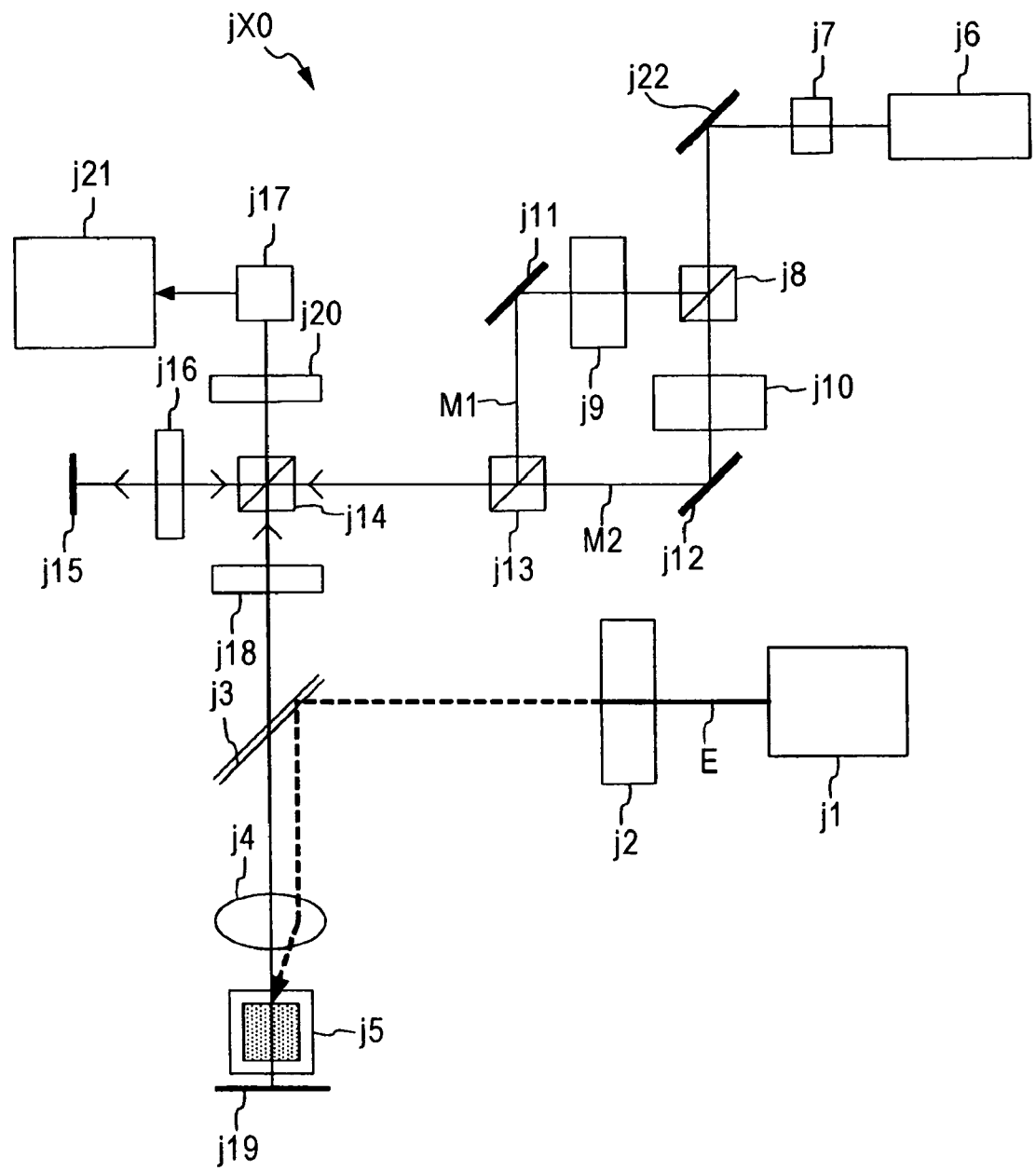
FIG. 17 is a schematic diagram illustrating an example of a known photothermal conversion measurement apparatus.
Figure 18A:
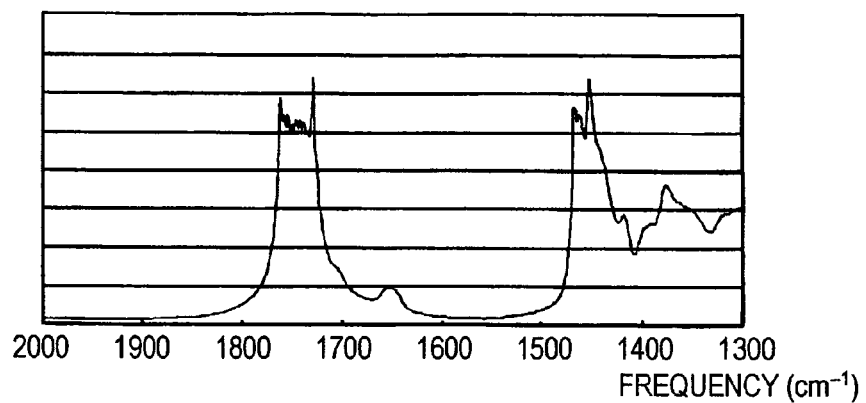
FIGS. 18A to 18C are graphs showing optical absorption wavelength ranges of a sample, a container member, and a solvent, respectively.
Figure 18B:
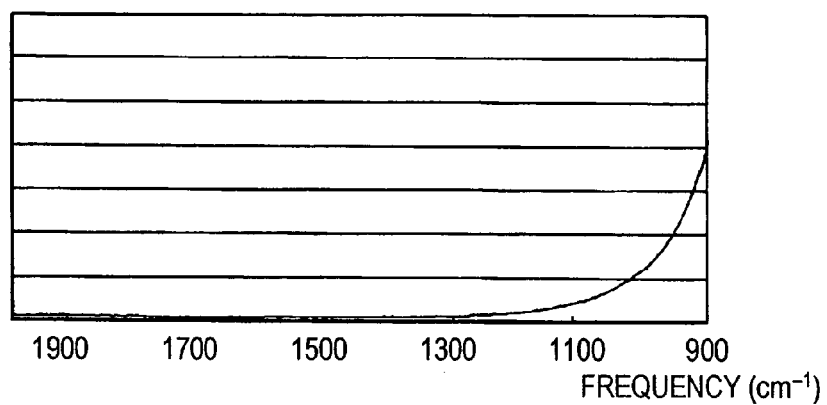
Figure 18C:
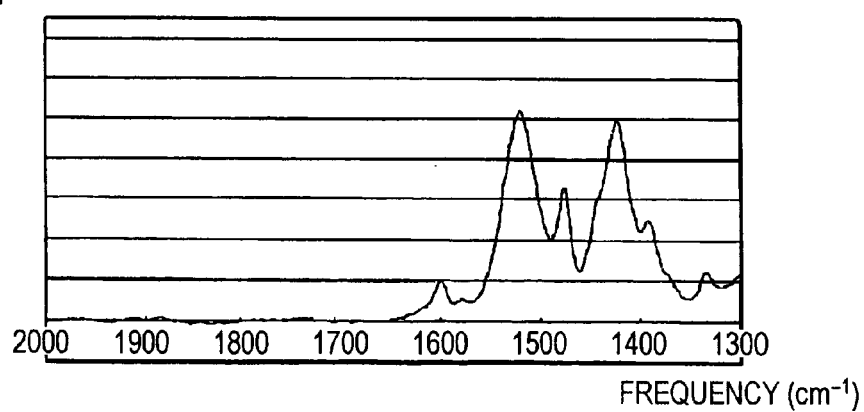
Figure 19:
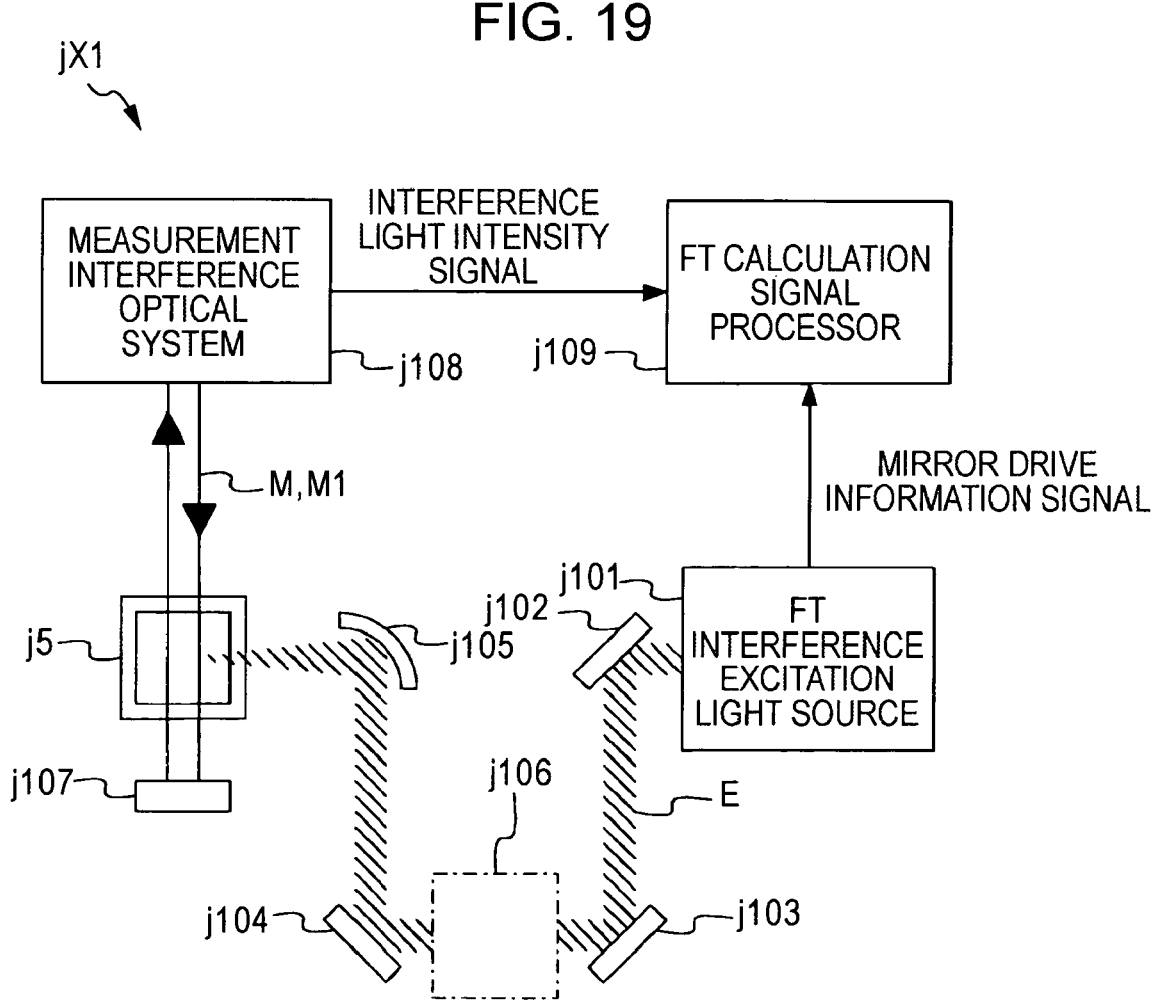
FIG. 19 is a schematic diagram of a photothermal conversion measurement apparatus according to an eighth embodiment of the present invention.
Figure 20:
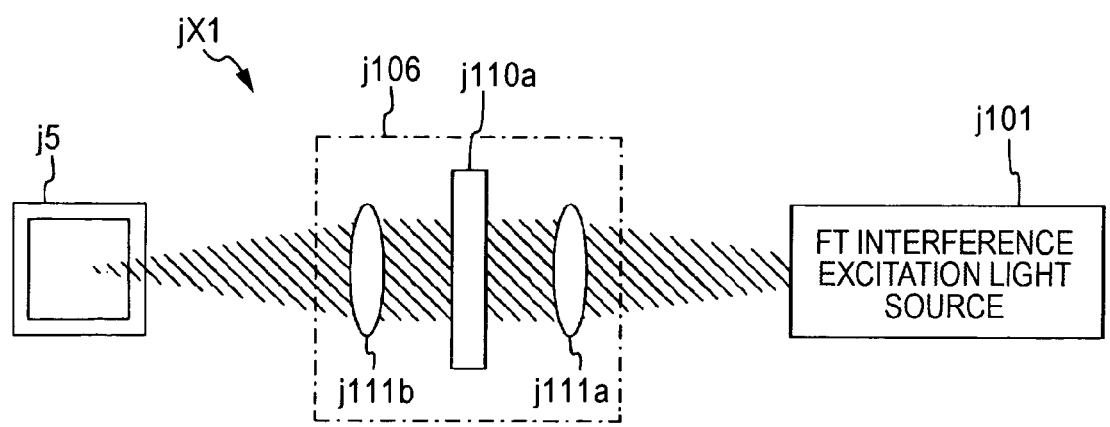
FIG. 20 is a schematic diagram illustrating a characteristic portion of the photothermal conversion measurement apparatus according to the eighth embodiment.
Figure 21:
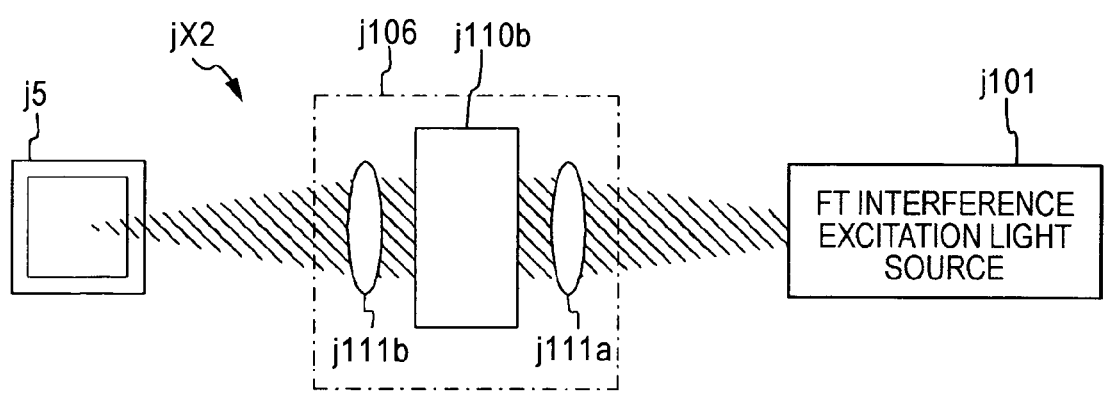
FIG. 21 is a schematic diagram illustrating a characteristic portion of a photothermal conversion measurement apparatus according to a ninth embodiment of the present invention.
Figure 22:
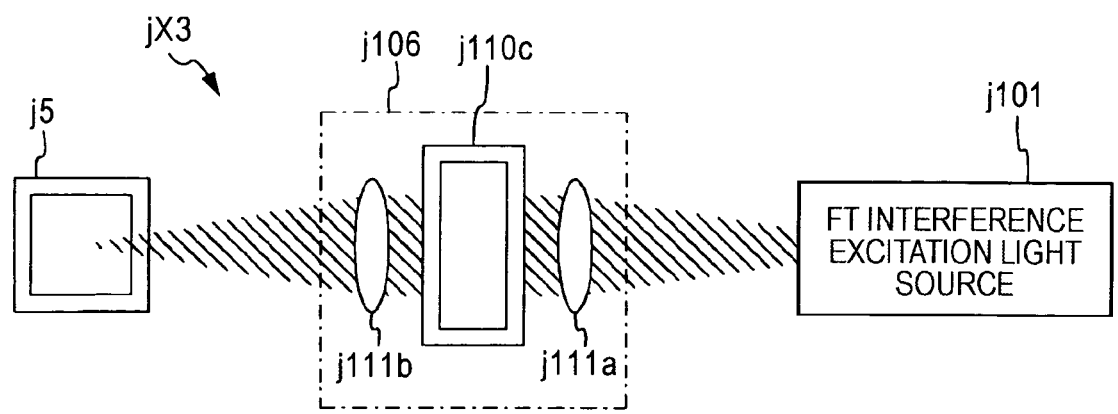
FIG. 22 is a schematic diagram illustrating a characteristic portion of a photothermal conversion measurement apparatus according to a tenth embodiment of the present invention.
Figure 23:
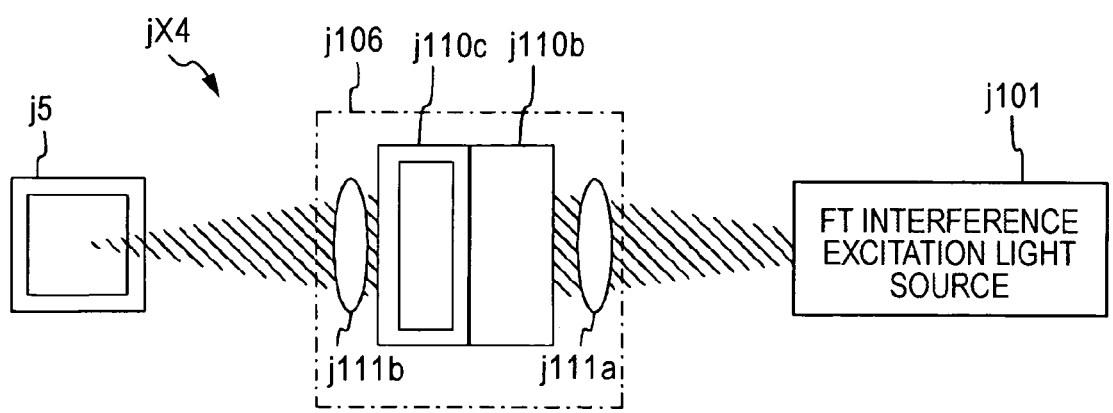
FIG. 23 is a schematic diagram illustrating a characteristic portion of a photothermal conversion measurement apparatus according to an eleventh embodiment of the present invention.

FIG. 1 is a schematic diagram of a photothermal conversion measurement apparatus X according to a first embodiment of the present invention. FIG. 2 is a schematic diagram of a measurement-position-scanning mechanism Z2 included in a photothermal conversion measurement apparatus according to a second embodiment of the present invention. FIG. 3 is a schematic diagram of a measurement-position-scanning mechanism Z3 included in a photothermal conversion measurement apparatus according to a third embodiment of the present invention. FIG. 4 is a schematic diagram of a photothermal conversion measurement apparatus hX according to a fourth embodiment of the present invention. FIG. 5 is a diagram showing the relationship between the optical path length of measurement light that travels between two high-reflection mirrors in the photothermal conversion measurement apparatus hX and the intensity of the measurement light reflected or transmitted by the high-reflection mirrors. FIG. 6 is a schematic diagram of an excitation-light output unit using Fourier spectrum that can be applied to the photothermal conversion measurement apparatus hX. FIG. 7 is a schematic diagram illustrating a photothermal conversion measurement apparatus iX0 as an example of a known photothermal conversion measurement apparatus. FIG. 8 is a schematic diagram of a characteristic portion of a photothermal conversion measurement apparatus iX1 according to a fifth embodiment of the present invention. FIG. 9 is another schematic diagram illustrating the characteristic portion of the photothermal conversion measurement apparatus iX1. FIG. 10 is a schematic diagram illustrating a characteristic portion of a photothermal conversion measurement apparatus iX2 according to a sixth embodiment of the present invention. FIG. 11 is a schematic diagram illustrating a characteristic portion of a photothermal conversion measurement apparatus iX3 according to a seventh embodiment of the present invention. FIG. 12 is a schematic diagram illustrating a sample cell i3' according to an embodiment of the present invention. FIG. 13 is a perspective view of a reflective mirror included in the sample cell i3'. FIGS. 14A and 14B are a front view and a side view, respectively, of a channel substrate included in the sample cell i3'. FIGS. 15A and 15B are a front view and a side view, respectively, of a cover substrate included in the sample cell i3'. FIG. 16 is a schematic diagram illustrating a sample cell i3" according to another embodiment of the present invention. FIG. 17 is a schematic diagram illustrating a photothermal conversion measurement apparatus jX0 as an example of a known photothermal conversion measurement apparatus. FIGS. 18A to 18C are graphs showing optical absorption wavelength ranges of a sample, a container member, and a solvent, respectively. FIG. 19 is a schematic diagram of a photothermal conversion measurement apparatus jX1 according to an eighth embodiment of the present invention. FIG. 20 is a schematic diagram illustrating a characteristic portion of the photothermal conversion measurement apparatus jX1. FIG. 21 is a schematic diagram illustrating a characteristic portion of a photothermal conversion measurement apparatus jX2 according to a ninth embodiment of the present invention. FIG. 22 is a schematic diagram illustrating a characteristic portion of a photothermal conversion measurement apparatus jX3 according to a tenth embodiment of the present invention. FIG. 23 is a schematic diagram illustrating a characteristic portion of a photothermal conversion measurement apparatus jX4 according to an eleventh embodiment of the present invention.

First Embodiment

A photothermal conversion measurement apparatus X according to a first embodiment of the present invention will be described below with reference to FIG. 1.

Excitation light P3 is emitted from a white light source 1 (e.g., a tungsten lamp), passes through a Fourier spectroscope 40, and is converted (periodically intensity-modulated) into chopped light with a predetermined period (chopping frequency f) by a chopper 2. Then, the optical path of the excitation light P3 is deflected by a measurement-position-changing mechanism Z1 and the excitation light P3 is incident on a liquid sample 5. The sample 5 absorbs the excitation light P3 and generates heat (photothermal effect) that causes a temperature change (increase), and accordingly the refractive index of the sample 5 is changed.

The Fourier spectroscope 40 is commonly known Fourier spectroscopic means including a beam splitter 41 that divides the light from the white light source 1 into two light components, a fixed mirror 42 that reflects one of the two light components, and a movable mirror 43 that reflects the other one of the two light components and that is moved at a predetermined period by a piezoelectric stage 43a. The two light components return to the beam splitter 41, where the two light components are combined and output toward the chopper 2 as the excitation light P3. Alternatively, the excitation light P3 may also be obtained by dividing light emitted from a white light source into spectral components with a spectroscope, intensity-modulating the spectral components using choppers with different frequencies, and collecting (combining) the spectral components.

A laser source 7 (for example, a He—Ne laser with an output of 1 mW) is an example of measurement-light-emitting means that outputs measurement light for irradiating the sample 5 to measure a change in the refractive index of the sample 5. The measurement light output from the laser source 7 enters a half-wave plate 8, where the plane of polarization thereof is adjusted, and is reflected by a mirror 23. Then, the measurement light is divided into two polarized waves P1 and P2 that are perpendicular to each other by a polarizing beam splitter (PBS) 9.

The polarized waves P1 and P2 enter acousto-optical modulators 10 and 11, respectively, where the optical frequencies of the polarized waves P1 and P2 are shifted (frequency conversion). Then, the polarized waves P1 and P2 are reflected by mirrors 12 and 13, respectively, and is combined by a PBS 14. The frequency difference $f_b$ between the polarized waves P1 and P2 that are perpendicular to each other is set to, for example, 30 MHz.

The polarized wave P2 in the combined measurement light passes through (is transmitted by) a PBS 15, is reflected by a mirror 18, and returns to the PBS 15. Since the polarized wave P2 passes through a quarter-wave plate 16 disposed between the PBS 15 and the mirror 18 twice before returning to the PBS 15, the plane of polarization of the polarized wave P2 is rotated by 90°. Therefore, the polarized wave P2 is reflected by the PBS 15 toward a photodetector 20.

The polarized wave P1 in the combined measurement light is reflected by the PBS 15, passes through a quarter-wave plate 17 and a lens 4, and is incident on the sample 5. The excitation light intersects the polarized wave P1 (measurement light) in the sample 5, and the position of intersection in the sample 5 defines a measurement position Q.

The polarized wave P1 passes through the sample 5, is reflected by a reflection mirror 6 provided on the back side of the sample 5 (i.e., the side opposite to the side at which the measurement light (polarized wave P1) is incident on the sample 5), and passes through the measurement position Q in the sample 5 again. Then, the polarized wave P1 passes through the lens 4 and the quarter-wave plate 17 and returns to the PBS 15. Since the polarized wave P1 passes through the quarter-wave plate 17 twice, the plane of polarization of the polarized wave P1 is rotated by 90°. Therefore, the polarized wave P1 passes through the PBS 15, where the polarized wave P1 and the polarized wave P2 are combined, and the combined light travels toward the photodetector 20.

A polarizing plate 19 is disposed between the PBS 15 and the photodetector 20. In the polarizing plate 19, the polarized wave P1 and the polarized wave P2 having different optical frequencies interfere with each other as observed light (measurement light) and reference light, respectively. The intensity of the thus obtained interference light is converted into an electric signal by the photodetector 20 (photoelectric conversion means). The signal value of this electric signal is hereafter called an interference light intensity. The electric signal (interference light intensity) is input and stored in a signal processor 21, such as a calculator, and the signal processor 21 calculates a phase change of the polarized wave P1 (measurement light). In other words, the phase change is measured by optical interferometry.

The interference light intensity S1 is expressed as follows:

$$S1 = C1 + C2 \cdot \cos(2\pi \cdot f_b \cdot t + \phi) \quad (1)$$

where C1 and C2 are constants determined by the transmittances of the sample 5 and optical systems including the PBSs, $\phi$ is the phase difference caused by the difference in the optical path length between the polarized waves P1 and P2, and $f_b$ is the frequency difference between the polarized waves P1 and P2. It is clear from Equation (1) that a change in the phase difference $\phi$ can be determined from a change in the interference light intensity S1 (i.e., a difference between the interference light intensity S1 obtained when the excitation light is not emitted or the intensity thereof is low and that obtained when the intensity of the excitation light is high). The signal processor 21 calculates the change in the phase difference $\phi$ from Equation (1).

The amount of absorption (amount of heat generated) varies depending on the amount of predetermined substance that absorbs the excitation light in the sample 5, and the refractive index varies in accordance with the amount of heat generated. In addition, the phase difference $\phi$ (optical path length of the polarized wave P1 in the sample 5) varies in accordance with the refractive index. Accordingly, the change in the phase difference $\phi$ (i.e., the phase change in the polarized wave P1) relative to the change in the excitation light is increased as the amount of the substance contained in the sample 5 is increased. Therefore, the change in the refractive index caused by the temperature change in the sample 5 can be determined by measuring the phase difference $\phi$, and accordingly the amount (concentration) of the substance in the sample can be analyzed.

More specifically, first, the photothermal conversion measurement apparatus X measures the change in the phase difference $\phi$ for a plurality of kinds of samples containing known amounts of predetermined substance (i.e., samples with known concentrations). The results of measurement are stored in the processing device 21 in association with the amounts of the substance in the form of a data table. Then, when a sample containing an unknown amount of the substance is measured, the signal processor 21 determines the amount of the substance by, for example, interpolation or the like using the above-mentioned data table on the basis of the change in the phase difference $\phi$ measured for this sample.

In the above-described photothermal conversion measurement apparatus X, the change in the refractive index caused by the photothermal effect of the sample 5 is determined by measuring the phase change of the measurement light (polarized wave P1) when the excitation light is incident on the sample 5 while the measurement light passes through (is transmitted by) the sample 5. In other words, the change in the refractive index is determined on the basis of the phase difference, that is, the comparative evaluation between the phase of the reference light (polarized wave P2) and the phase of the measurement light (polarized wave P1). Therefore, even if, for example, the position of the photodetector 20, the intensity of the measurement light, and the intensity distribution of the measurement light differ for each apparatus, the change in the refractive index (property change) of the sample can be stably measured with high optical accuracy without being influenced by such factors as long as they to not vary during the measurement.

In addition, in the photothermal conversion measurement apparatus X, the measurement light (polarized wave P1) is reflected by the reflection mirror 6 (light-reflecting means) disposed on the back side of the sample 5, so that the measurement light (polarized wave P1) passes through the sample 5 twice in opposite directions. Therefore, the measurement sensitivity of the change in the phase difference $\phi$ can be doubled compared to that in the case in which the measurement light passes through the sample only once. In addition, the output of the excitation light is not increased and the S/N ratio is not reduced.

Since the excitation light is intensity-modulated with the frequency f, the refractive index of the sample 5 varies with the frequency f. Accordingly, the optical path length of the polarized wave P1 also varies with the frequency f (optical path length of the polarized wave P2 is constant), and the phase difference $\phi$ also varies with the frequency f. Therefore, when the change in the phase difference $\phi$ is measured (calculated) on the basis of a component with the frequency f (periodic component with the same period as the intensity modulation period of the excitation signal), the influence of noise that does not have a component with the frequency f can be eliminated and it becomes possible to detect only the change in the refractive index of the sample 5.

Accordingly, the S/N ratio in the measurement of the phase difference $\phi$ can be increased.

The change in the refractive index of the sample caused by the photothermal effect also differs depending on the wavelength of the excitation light. In addition, the photothermal effect caused by the excitation light having a certain wavelength and the change in the refractive index of the sample caused by the photothermal effect differ depending on the kind of substance contained in the sample.

Accordingly, when the excitation light is emitted with a plurality of different wavelengths and the change in the phase difference $\phi$ is measured for each wavelength, the kind and amount of the substance contained in the sample can be determined (evaluated) from the distribution of the change in the phase difference $\phi$. However, in such a case, the measurement must be performed for each wavelength of the excitation light and the measurement efficiency is low since the measurement time is increased and the process becomes complex.

In the photothermal conversion measurement apparatus X, the Fourier spectroscope 40 is used to obtain the excitation light P3 with an interference waveform (interferogram). Therefore, by subjecting the detection signal of the phase change of the measurement light P1 to Fourier transformation with a period synchronized with a displacement period of the piezoelectric stage 43a, the change in the refractive index of the sample caused by the measurement light with a plurality of different wavelengths (spectrum) can be obtained by a single measurement. Thus, the measurement efficiency can be increased.

The spectrum measurement based on the Fourier spectrum is described in detail in Japanese Unexamined Utility Model Registration Application Publication No. 5-23072, and detailed explanations thereof are thus omitted here.

Next, the measurement-position-changing mechanism Z1 will be described below.

The measurement-position-changing mechanism Z1 is used to change the measurement position Q at which the path of the beam-shaped measurement light P1 passes through (intersects) a excitation section of the beam-shaped excitation light P3 (path of the beam-shaped excitation light P3 in this case) in the sample 5. The measurement position Q is changed by moving the optical path of the excitation light P3 while the path of the measurement light P1 is fixed. The measurement-position-changing mechanism Z1 is an example of measurement-position-changing means and optical-path-changing means.

The measurement-position-changing mechanism Z1 includes a movable mirror 31 that reflects the excitation light P3 toward the sample 5 such that the excitation light P3 is incident on the sample 5 in a direction inclined with respect to the measurement light P1 (example of an intersecting direction); a piezoelectric stage 30 that linearly moves the movable mirror 31 (in a direction parallel to the measurement light P1 in this case); and a fixed mirror 32 that guides the excitation light P3 from the chopper 2 to the movable mirror 31.

The measurement-position-changing mechanism Z1 causes the excitation light P3 to be incident on the sample 5 in a direction inclined with respect to the incident direction of the measurement light P1. The incident position of the excitation light P3 on the sample 5 changes as the piezoelectric stage 30 moves the movable mirror 31. Accordingly, the measurement position Q at which the path of the measurement light P1 passes through the excitation section of the excitation light P3 in the sample 5 changes in the depth direction of the sample 5 (direction in which the measurement light P1 travels). Thus, the measurement-position-changing mechanism Z1 functions as the optical-path-changing means. The incident direction of the excitation light P3 may also be perpendicular to the measurement light P1.

A control unit (not shown) controls the measurement-position-changing mechanism Z1 and the signal processor 21. The measurement-position-changing mechanism Z1 is controlled so as to change the measurement position Q, and the signal processor 21 is controlled so as to measure the phase change in the measurement light P1 (polarized wave) that passes through the sample 5 by optical interferometry for each measurement position Q set by the measurement-position- changing mechanism. The signal processor 21 is an example of light-measuring means.

Accordingly, the measurement can be performed while moving the measurement position Q in the sample 5. Therefore, the distribution of the property change caused by the photothermal effect in the sample 5 in the depth direction thereof can be measured.

The above-described measurement-position-changing mechanism Z1 linearly moves the movable mirror 31 to change the incident position of the excitation light P3 on the sample 5. However, the present invention is not limited to this. For example, a measurement-position-changing mechanism that rotates the movable mirror 31 to change the incident position and the incident angle of the excitation light P3 on the sample 5 may also be used. In addition, a measurement-position-changing mechanism that rotates the movable mirror 31 around a predetermined position to change only the incident direction of the excitation light P3 on the sample 5 while the incident position does not change may also be used.

Second Embodiment

A measurement-position-changing mechanism Z2 included in a photothermal conversion measurement apparatus according to a second embodiment of the present invention will be described below with reference to FIG. 2.

Photothermal conversion measurement apparatuses according to second and third embodiments are similar to the above-described photothermal conversion measurement apparatus X except for the structure of the measurement-position-changing mechanism.

Similar to the measurement-position-changing mechanism Z1, the measurement-position-changing mechanism Z2 shown in FIG. 2 also changes a measurement position Q by moving an optical path of excitation light P3 while a path of measurement light P1 is fixed.

More specifically, the measurement-position-changing mechanism Z2 (example of second optical-path-changing means) includes a half mirror 3, a lens 4, and a lens-moving unit 50 (example of lens-moving means). The half mirror 3 is placed on the path of the beam-shaped measurement light P1 that travels toward a liquid sample 5 and allows the measurement light P1 to pass therethrough. In addition, the half mirror 3 reflects (deflects) the excitation light P3 that has a larger spot diameter than that of the measurement light P1 and causes the excitation light P3 to travel in the same direction as the incident direction of the measurement light P1. The lens 4 focuses the excitation light P3 reflected by the half mirror 3 when the excitation light P3 passes through the lens 4 toward the sample 5. The lens-moving unit 50 moves the lens 4 in the same direction as the incident direction of the measurement light P1 with a piezoelectric stage or the like.

The lens 4 is positioned such that the measurement light P1 passes through the center thereof. Although not shown in the figure, the excitation light P3 is guided to the half mirror 3 by optical systems including reflection mirrors and the like. The focus position (light-collecting position) of the excitation light P3 in the sample 5 changes when the lens-moving unit 50 moves the lens 4.

In this case, excitation hardly occurs in a region where the spot diameter of the excitation light P3 is large in the sample 5, and only a focus position (light-collecting position) of the excitation light P3 functions as a major excitation section. The focus position moves along the path of the measurement light P1 when the lens 4 is moved, and accordingly the excitation section (i.e., the measurement position Q) is moved in the depth direction of the sample 5.

Although the measurement light P1 also passes through the lens 4 that moves, the influence of the movement of the lens 4 on the measurement light P1 can be ignored if the spot size of the beam-shaped measurement light P1 is sufficiently small.

Also in this case, the measurement can be performed while moving the measurement position Q in the sample 5, and therefore the distribution of the property change caused by the photothermal effect in the sample 5 in the depth direction thereof can be measured.

Third Embodiment

A measurement-position-changing mechanism Z3 included in a photothermal conversion measurement apparatus according to a third embodiment of the present invention will be described below with reference to FIG. 3.

The measurement-position-changing mechanism Z3 shown in FIG. 3 changes a measurement position Q by moving the position of a liquid sample 5 while paths of measurement light P1 and excitation light P3 are both fixed. The measurement-position-changing mechanism Z3 includes a support 22 for supporting the sample 5 and a sample-moving unit 51 (example of sample-moving means) including a piezoelectric stage or the like that moves the support 22 along the incident direction of the measurement light P1 on the sample 5.

In the structure shown in FIG. 3, the support 22 of the sample 5 is moved while the excitation light P3 is incident on the sample 5 in a direction inclined with respect to the incident direction of the measurement light P1. Alternatively, however, the support 22 of the sample 5 may also be moved while the excitation light P3 is focused with a lens on a predetermined position on the path of the measurement light P1, as shown in FIG. 2.

Also in this case, the measurement can be performed while moving the measurement position Q in the sample 5, and therefore the distribution of the property change caused by the photothermal effect in the sample 5 in the depth direction thereof can be measured.

The measurement-position-changing mechanism Z3 may also be used in combination with the measurement-position-changing mechanism Z1 or Z2. In such a case, the total adjustable range of the measurement position Q can be increased even if the adjustable range of each measurement-position-changing mechanism including a piezoelectric stage or the like is small. In addition, one of the mechanisms may be used for rough adjustment while the other is used for fine adjustment.

Fourth Embodiment

Next, a photothermal conversion measurement apparatus hX according to a fourth embodiment of the present invention will be described below.

The photothermal conversion measurement apparatus hX is used to measure a property change of a sample caused by a photothermal effect when the sample is irradiated with excitation light on the basis of measurement light that passes through the sample. In the photothermal conversion measurement apparatus hX, two high-reflection mirrors, which are arranged so as to face each other across the sample, repeatedly reflect the measurement light incident on the sample between the high-reflection mirrors along one axis while allowing the measurement light to pass through the sample. Then, the intensity of the measurement light that passes through at least one of the two high-reflection mirrors is detected by a light-intensity detector.

The photothermal conversion measurement apparatus hX will be described below with reference to FIG. 4.

As shown in FIG. 4, the photothermal conversion measurement apparatus hX includes a spectral excitation light source h1, a chopper h2, mirrors h3a and h3b, a lens h20, a laser source h6 that emits measurement light, a beam splitter h7, high-reflection mirrors h8 and h9, photodetectors h12 and h13, a mirror-moving mechanism h10, a displacement controller h11, and a signal processor h14.

Excitation light is emitted from the spectral excitation light source h1, which is a system including a white light source, such as a halogen lamp, that emits white light and variable spectroscopic means that outputs light obtained by dividing the white light into spectral components with a diffraction grating as the excitation light and that is capable of varying the wavelength range of the excitation light. The excitation light is converted (periodically intensity-modulated) into chopped light with a predetermined period (chopping frequency f) by the chopper h2 (example of intensity-modulating means). Then, the excitation light is reflected by the mirrors h3a and h3b, passes through the lens h20, and is incident on a liquid sample h5 contained in a cell h15, which is a transparent container made of silica glass or the like. Accordingly, the sample h5 absorbs the excitation light and generates heat (photothermal effect) that causes a temperature change (increase), and accordingly the refractive index of the sample h5 is changed.

The change in the refractive index of the sample h5 caused by the photothermal effect differs depending on the wavelength of the excitation light. In addition, the photothermal effect caused by the excitation light having a certain wavelength and the change in the refractive index of the sample caused by the photothermal effect differ depending on the kind of substance contained in the sample. Accordingly, a spectral component having a wavelength to be measured is obtained by the spectral excitation light source h1.

Alternatively, as shown in FIG. 6, a commonly known excitation-light output unit using Fourier spectrum may also be used. In this unit, light emitted from a white light source h40 is divided into two components by a beam splitter h41, and the two components are respectively reflected by a fixed mirror h42 and a movable mirror h43. Accordingly, the two components return to the beam splitter h41, and are combined and output as the excitation light.

The laser source h6 (for example, a He—Ne laser with an output of 1 mW) outputs measurement light for irradiating the sample h5 to measure a change in the refractive index of the sample h5. The measurement light output from the laser source h6 passes through the beam splitter h7. The high-reflection mirrors h8 and h9 (example of light-reflecting means) are arranged so as to face each other in parallel across the sample h5 (in front of and behind the sample h5). The major part of the measurement light that passes through the beam splitter h7 is reflected by one of the high-reflection mirrors h8 and h9 that is disposed in front of the sample h5 (hereafter called a first high-reflection mirror h8). The remaining part of the measurement light passes through the first high-reflection mirror h8 and is incident on the sample h5. The measurement light incident on the sample h5 is repeatedly reflected between the other high-reflection mirror h9 that is disposed behind the sample h5 (hereafter called a second high-reflection mirror h9) and the first high-reflection mirror h8 along one axis such that the measurement light passes through the sample h5 multiple times. At this time, a small part of the measurement light that is repeatedly reflected between the two high-reflection mirrors h8 and h9 passes through the high-reflection mirrors h8 and h9 each time the measurement light reaches the high-reflection mirrors h8 and h9.

Accordingly, the measurement light that passes through the first high-reflection mirror h8 in a direction away from the sample h5 (upward in FIG. 4) is a superposition of measurement-light components that travel between the mirrors h8 and h9 different numbers of times. The thus obtained measurement light is combined with the measurement light that is reflected by the first high-reflection mirror h8, and the combined measurement light (hereafter called reflection-side measurement light) travels toward the beam splitter h7.

Similarly, the measurement light that passes through the second high-reflection mirror h9 in a direction away from the sample h5 (downward in FIG. 4) is also a superposition of measurement-light components that travel between the mirrors h8 and h9 different numbers of times. The thus obtained measurement light is hereafter called transmission-side measurement light.

The reflection-side measurement light including light that passes through the first high-reflection mirror h8 in the direction away from the sample h5 is reflected by the beam splitter h7 and is received by the photodetector h13 (hereafter called a first photodetector), which is an example of light-intensity-detecting means. Then, a signal (light intensity signal) representing the intensity of the reflection-side measurement light is input to the signal processor h14.

The signal processor h14 is a signal processing system including an input interface for receiving the light intensity signal detected by the first photodetector h13. The signal processor h14 extracts a periodic component of the light intensity signal that has the same period as the intensity modulation period at which the excitation light is intensity-modulated by the chopper h2, and outputs the extracted periodic component to another measurement processor as a photothermal conversion signal. The signal processor h14 is an example of periodic-component-extracting means.

Since the excitation light is intensity-modulated with the frequency f, the refractive index of the sample h5 varies with the frequency f. Accordingly, the light intensity signal detected by the first photodetector h13 also varies with the frequency f. Therefore, when the light intensity signal is measured (calculated) on the basis of a component with the frequency f (a periodic component with the same period as the intensity modulation period of the excitation signal), the influence of noise that does not have a component with the frequency f can be eliminated.

The transmission-side measurement light that passes through the second high-reflection mirror h9 in the direction away from the sample h5 is received by the other photodetector h12 (hereafter called a second photodetector), which is an example of light-intensity-detecting means. Then, a light intensity signal obtained by the second photodetector h12 is input to the displacement controller h11.

The displacement controller h11 controls the mirror-moving mechanism h10, which supports the second reflection mirror h9 and automatically moves the support position of the second reflection mirror h9 along an optical axis of the measurement light, on the basis of the detection signal obtained by the second photodetector h12 (light-intensity-detecting means). More specifically, the mirror-moving mechanism h10 is controlled such that the distance between the two high-reflection mirrors h8 and h9 is automatically adjusted so as to reduce variation in the detection signal from the second photodetector h12 (light-intensity-detecting means). The displacement controller h11 is an example of distance-adjusting means.

In the following description, an optical path length L refers to a one-way distance by which the measurement light travels between the two high-reflection mirrors h8 and h9. The relationships between the optical path length L and the intensity P1 of the reflection-side measurement light from the first high-reflection mirror h8 and between the optical path length L and the intensity P2 of the transmission-side measurement light P2 that passes through the second high-reflection mirror h9 will be described below with reference to FIG. 5.

As described above, the transmission-side measurement light is a superposition of measurement-light components that travel between the mirrors h8 and h9 different numbers of times (hereafter called multiple-reflection light components). Therefore, as shown in FIG. 5, the multiple-reflection light components are in phase with one another and reinforce one another (resonate with one another) when the optical path length L satisfies $L=n\cdot\lambda/2$ (n is a positive integer and $\lambda$ is the wavelength of the light components between the two mirrors). At this time, the light intensity P2 of the transmission-side measurement light reaches the maximum intensity P2max. If the optical path length L is even slightly changed from $L=n\cdot\lambda/2$, the intensity P2 of the transmission-side measurement light is considerably reduced since a larger phase shift occurs as the number of times of reflection between the mirrors is increased. When the reflectance of the high-reflection mirrors h8 and h9 is R (0 to 1) and the optical path length that satisfy the relationship $L=n\cdot\lambda/2$ is Ln ($=n\cdot\lambda/2$), a range $\Delta L$ of the optical path length (hereafter called a optical path length range) centered on the optical path length Ln in which the intensity P2 of the transmission-side measurement light varies is calculated as follows:

$$\Delta L = Ln \cdot \pi \cdot R^{1/2}/(1-R) \quad (2)$$

As the reflectance R of the high-reflection mirrors h8 and h9 is increased and as the optical path length Ln between the mirrors is reduced, the optical path length range ΔL is reduced, which means that a small change in the optical path length can be measured with high sensitivity.

The intensity P1 of the reflection-side measurement light is calculated from the energy conservation law as a value equal or close to a difference between the intensity P1max, which is approximately equal to the initial intensity of the measurement light, and the intensity P2 of the transmission-side measurement light (P1≈P1max−P2).

The property shown in FIG. 5 is utilized in the present embodiment. An example of the measurement procedure according to the present embodiment will be described below.

Step 1

First, the high-reflection mirrors h8 and h9, which are arranged so as to face each other across the sample h5, repeatedly reflect the measurement light incident on the sample h5 along one axis while allowing the measurement light to pass through the sample h5. In this state, the signal processor h14 determines the intensity P1 of the reflection-side measurement light on the basis of the signal received from the first photodetector h13 that detects the reflection-side measurement light while the sample h5 is not irradiated with the excitation light.

Then, the distance between the two high-reflection mirrors h8 and h9 is adjusted by a position-adjusting mechanism (not shown) such that the intensity P1 is at the minimum intensity P1min (≈P1max−P2max) or the middle intensity between the minimum intensity P1min and the maximum intensity P1max. The distance between the two high-reflection mirrors h8 and h9 may also be adjusted such that the intensity P2 detected by the second photodetector h12 is at the maximum intensity P2max or the middle intensity between the maximum intensity P2max and the minimum intensity thereof.

At this time, if the intensity P2 (signal) of the reflection-side measurement light detected by the second photodetector h12 varies (intensity P1 of the detection signal detected by the first photodetector h13 also varies in this case), the second high-reflection mirror h9 is moved by a distance corresponding to the amount of variation by the displacement controller h11 and the mirror-moving mechanism h10. More specifically, the distance between the two high-reflection mirrors h8 and h9 is adjusted so as to reduce the variation in the detection signal obtained by the second photodetector h12. The adjustment using the displacement controller h11 and the mirror-moving mechanism h10 is continued during the measurement.

Step 2

Next, while the above-described position adjustment of the two high-reflection mirrors h8 and h9 is being performed, the signal processor h14 stores the intensity of the reflection-side measurement light detected by the first photodetector 13 in storing means each time the state in which the sample h5 is irradiated with the excitation light is changed (for example, between the state in which the sample h5 is irradiated with the excitation light that is intensity-modulated by the chopper h2 and the state in which the sample h5 is not irradiated). This step is an example of a light-intensity-detecting step.

When the sample h5 is irradiated with the excitation light, the refractive index of the sample h5 changes due to the photothermal effect, and accordingly the optical path length L changes. As a result, even a small change in the refractive index of the sample h5 causes a relatively large change in the intensity of the reflection-side measurement light.

Step 3

Next, the signal processor h14 outputs a photothermal conversion signal to a measurement processor (not shown), the photothermal conversion signal representing the intensity of the reflection-side measurement light obtained when the state in which the sample h5 is irradiated with the excitation light is changed.

The measurement processor has, for example, a data table, a conversion equation, or the like that represents the relationship between the photothermal conversion signal and the change in the refractive index of the sample h5 based on the result of measurement of a reference sample h5. Accordingly, the measurement processor determines the change in the refractive index (property change) caused by the photothermal effect of the sample h5 on the basis of the photothermal conversion signal received from the signal processor h14 using the data table, the conversion equation, or the like. This is an example of a property-change-measuring step.

Accordingly, the property change (change in the refractive index) caused by the photothermal effect of the sample h5 can be measured with high sensitivity. In addition, the high-sensitivity measurement can be performed with an apparatus having a very simple structure, as shown in FIG. 4.

In addition, when the wavelength range of the excitation light is changed by the spectral excitation light source h1 and the above-described steps 2 and 3 (detection of light intensity) are performed each time the wavelength range is changed, the absorption spectral property of the sample can be easily performed.

In the above-described measurement process, the photothermal conversion property of the sample h5 is measured on the basis of the intensity P1 of the reflection-side measurement light from the first high-reflection mirror h8. However, since the sum of the intensity P1 of the reflection-side measurement light and the intensity P2 of the transmission-side measurement light is constant (≈P1max), the photothermal conversion property of the sample h5 may also be measured on the basis of the intensity P2 of the transmission-side measurement light that passes through the second high-reflection mirror h9. More specifically, the property evaluation of the sample h5 is performed on the basis of the intensity of the measurement light that is reflected or transmitted by at least one of the two high-reflection mirrors h8 and h9 in a direction away from the sample h5.

When disturbance, such as vibration, in the measurement environment does not largely vary during the measurement, disturbance components may be cancelled (variation in the detection signal may be reduced) by the above-described method. More specifically, the variation period and the amount of variation of the detection signal obtained by one of the photodetectors h12 and h13 is detected in advance and automatic adjustment of the distance between the two high-reflection mirrors h8 and h9 is continuously performed under conditions (frequency and amount of movement) determined on the basis of the obtained detection result. If the disturbance, such as vibration, varies with time, the detection signal obtained by the second photodetector h12 may be monitored during the measurement in which the excitation light is incident on the sample h5 and the mirror-moving mechanism h10 may be feedback controlled by the displacement controller h11 so as to reduce the variation. In this case, the variation must, of course, be evaluated on the basis of a signal obtained by removing a component with the same period as the intensity modulation period at which the excitation light is intensity-modulated by the chopper h2 from the detection signal obtained by the second photodetector h12.

The structure of the fourth embodiment may be used in combination with the first to third embodiments.

Next, photothermal conversion measurement apparatuses according to fifth to seventh embodiments of the present invention will be described below. First, the structure of a known photothermal conversion measurement apparatus iX0 will be described below with reference to FIG. 7.

The fifth to seventh embodiments of the present invention are based on the known photothermal conversion measurement apparatus iX0 shown in FIG. 7. As shown in FIG. 7, the photothermal conversion measurement apparatus iX0 includes a light source i1, a chopper i2, a measurement optical system i4, a mirror i5, and a signal processor i6. A sample cell i3 containing a liquid sample to be analyzed is placed at a predetermined position. The sample cell i3 is a container for containing the sample, and includes a solvent bath filled with the sample that is dissolved in a solvent.

The sample in the sample cell i3 is irradiated with excitation light E emitted from the light source i1. The excitation light E is converted into chopped light by the chopper i2 before being incident on the sample cell i3. When the excitation light E is incident on the sample contained in the sample cell i3, the sample is excited and generates heat.

The sample in the sample cell i3 is also irradiated with measurement light M that is emitted from the measurement optical system i4 to analyze the sample. The measurement light iM is reflected by the mirror i5, passes through the sample cell i3, and returns to the measurement optical system i4.

When the temperature of the sample increases, the refractive index of the sample changes. The change in the refractive index is detected by the measurement optical system i4 as the phase change of the measurement light M. Accordingly, the property change of the sample in the sample cell 3 caused by the photothermal effect can be measured by irradiating the sample with the measurement light M.

The signal processor i6 receives a predetermined reference signal from the chopper i2. The reference signal represents the period and timing at which the excitation light is converted into the chopped light.

The signal processor i6 performs a synchronization signal process of the laser signal using the above-described reference signal and obtains a detection signal having an intensity that is proportional to the amount of temperature change in the solvent. Thus, the refractive index of the sample is measured on the basis of the intensity change of the detection signal and the amount of substance contained in the sample is evaluated quantitatively.

Next, photothermal conversion measurement apparatuses according to fifth to seventh embodiments of the present invention will be described below. Components similar to those included in the known photothermal conversion measurement apparatus shown in FIG. 7 are denoted by the same reference numerals and explanations thereof are thus omitted.

The structure of the fifth to seventh embodiments may be applied in combination with the structures of the first to fourth embodiments.

Fifth Embodiment

FIG. 8 is a schematic diagram of a photothermal conversion measurement apparatus iX1 according to a fifth embodiment of the present invention. FIG. 9 is a schematic diagram illustrating a characteristic portion of the photothermal conversion measurement apparatus iX1. The photothermal conversion measurement apparatus iX1 according to the fifth embodiment of the present invention will be described below with reference to FIGS. 8 and 9.

As shown in FIGS. 8 and 9, in the photothermal conversion measurement apparatus iX1, excitation light E is emitted from a light source i1 toward a sample cell i3, passes through the sample cell i3, and is reflected (deflected or redirected) toward the sample cell i3 by a reflection mirror i7a (example of excitation-light-deflecting means).

The reflection mirror i7a (example of excitation-light-deflecting means) shown in FIG. 8 is a plane mirror, and is arranged to be perpendicular to the incident direction of the excitation light E. Accordingly, the excitation light E reflected by the reflection mirror i7a is incident on the sample in the sample cell i3 at the same portion as the portion at which the excitation light E is incident on the sample the first time.

The reflection mirror i7a is supported by a position-adjusting mechanism (not shown) such that the position of the reflection mirror i7a can be moved upstream or downstream in the incident direction of the excitation light E.

Since the excitation light E emitted from the light source il is incident on the sample cell twice at the same portion, the density of the excitation light is increased in the sample cell. Therefore, the amount of light absorbed by the sample increases and a detection signal with a high intensity can be input to the signal processor i6.

Sixth Embodiment

FIG. 10 is a schematic diagram illustrating a characteristic portion of a photothermal conversion measurement apparatus iX2 according to a sixth embodiment of the present invention. The photothermal conversion measurement apparatus iX2 will be described below with reference to FIG. 10.

As shown in FIG. 10, the photothermal conversion measurement apparatus iX2 includes a pair of identical lenses i8a and i8b in addition to a reflection mirror i7a similar to the above-described reflection mirror i7a. The lenses i8a and i8b are respectively disposed on the upstream and downstream of a sample cell i3 in the incident direction of excitation light E.

When the excitation light E emitted from a light source i1 is incident on the sample cell i3, the excitation light E is collected by the upstream lens i8a (example of light-collecting means) so that the diameter thereof is reduced. The excitation light E is incident on the sample cell i3 at a position near the focal point of the lens i8a.

After the excitation light E passes through the sample cell i3, the diameter thereof is gradually increased. Then, the excitation light E is refracted by the downstream lens i8b so that the diameter and traveling direction of the excitation light E are set to those of the excitation light E before entering the lens i8a.

The excitation light E refracted by the lens i8b is reflected by the reflection mirror i7a and is incident on the sample cell i3 again after the excitation light E is collected by the lens i8b.

Similar to the above-described reflection mirror i7a, the lenses i8a and i8b are also supported by a position-adjusting mechanism (not shown) such that the position thereof can be moved upstream or downstream in the incident direction of the excitation light E.

In this example, the excitation light E is incident on the sample cell i3a after the excitation light E is collected by the lenses i8a and i8b to increase the density thereof. Therefore, this structure is suitable for the case in which a small target region in the sample is to be analyzed, and the small target region can be irradiated with high-density excitation light.

Seventh Embodiment

FIG. 11 is a schematic diagram illustrating a characteristic portion of a photothermal conversion measurement apparatus iX2 according to a seventh embodiment of the present invention. The photothermal conversion measurement apparatus iX2 will be described below with reference to FIG. 11.

As shown in FIG. 11, in the photothermal conversion measurement apparatus iX2, excitation light E is emitted from a light source i1 toward a sample cell i3, passes through the sample cell i3, and is reflected (redirected) toward the sample cell i3 by a reflection mirror i7b. In addition, a lens i8a is disposed on the upstream of the sample cell i3 in the incident direction of the excitation light E. The reflection mirror i7b (example of light-collecting means) includes a concave mirror surface on the side facing the sample cell i3.

When the excitation light E emitted from a light source i1 is incident on the sample cell i3, the excitation light E is collected by the upstream lens i8a so that the diameter thereof is reduced. The excitation light E is incident on the sample cell i3 at a position near the focal point of the lens i8a.

After the excitation light E passes through the sample cell i3, the diameter thereof is gradually increased. Then, the excitation light E is reflected by the reflection mirror i7b toward the sample cell i3 such that the excitation light E is collected.

Also in this case, the excitation light E is collected by the lens i8a and the reflection mirror i7b so that the density thereof is increased. Accordingly, the sample can be irradiated with high-density excitation light. In this embodiment, the reflection mirror i7b (concave mirror) serves both as excitation-light-deflecting means for redirecting the excitation light E toward the sample cell i3 and light-collecting means for collecting the excitation light E that travels toward the sample cell i3.

In the above-described fifth to seventh embodiments, an optical system for redirecting the excitation light E toward the sample cell i3 is disposed at a position separated from the sample cell i3. However, the present invention is not limited to this.

More specifically, according to the present invention, the above-described optical system (reflection mirror substrate i7c in the structure described below) may be integrated with a sample cell.

FIG. 12 is a schematic diagram illustrating a sample cell i3' according to an embodiment of the present invention and a section of a photothermal conversion measurement apparatus around the sample cell i3'. FIG. 13 is a perspective view of a reflection mirror substrate i7c included in the sample cell i3'. FIGS. 14A and 14B are a front view and a side view, respectively, of a channel substrate i10 included in the sample cell i3'. FIGS. 15A and 15B are a front view and a side view, respectively, of a cover substrate i11 included in the sample cell i3'. The sample cell i3' will be described below with reference to FIGS. 12 to 15.

As shown in FIG. 12, the sample cell i3' includes the reflection mirror substrate i7c, the channel substrate i10 that corresponds to a known sample cell, and the cover substrate i11 that are integrated with one another. More specifically, the sample cell i3' is obtained by laminating three substrates (the reflection mirror substrate i7c, the channel substrate i10, and the cover substrate i11) having small structures (a concave portion, a groove, and a hole) formed by micromachining processes used for manufacturing micro-electro-mechanical system (MEMS) devices.

FIG. 13 is a perspective view of the reflection mirror substrate i7c. The reflection mirror substrate i7c is a substrate of silica or the like in which a hemispherical concave portion and is formed by micromachining, and a concave mirror i9 is formed by adhering an aluminum film on the concave portion.

An example of a micromachining process suitable for forming the concave portion is etching, and silica, glass, etc., that show isotropy in such a micromachining process are preferably used as the material of the reflection mirror substrate i7c. In addition, the film used for forming the concave mirror i9 is not limit to the aluminum film. Preferably, a suitable metal film is selected in accordance with the wavelength range of the excitation light E. For example, an Au film is preferably used for the infrared excitation light.

FIGS. 14A and 14B are a front view and a side view, respectively, of the channel substrate i10. The channel substrate i10 is made of silica or the like and has a solvent bath i12 that extends along the length of the channel substrate i10 on one side thereof. The solvent bath i12 is also formed by micromachining.

The material of the channel substrate i10 is not limited to silica, and various materials may be used as long as they are capable of transmitting the excitation light E and measurement light M and suitable for micromachining.

FIGS. 15A and 15B show the front view and the side view, respectively, of the cover substrate i11. The cover substrate i11 covers the solvent bath i12 formed in the channel substrate i10. The cover substrate i11 is made of silica or the like and has an injection channel i13 that extends in the thickness direction of the cover substrate i11 and through which the solvent and sample are injected into the solvent path i12.

The material of the channel substrate i11 is not limited to silica, and various materials may be used as long as they are capable of transmitting the excitation light E and suitable for micromachining. For example, silica may be used when visible light is used as the excitation light E and CaF2 (calcium fluoride) may be used when the infrared light is used as the excitation light E.

As shown in FIG. 12, the sample cell i3' is obtained by adhering the reflecting side of the reflection mirror substrate i7c (side in which the concave mirror 9 is formed) to the side of the channel substrate i10 opposite to the side in which the solvent bath i12 is formed and adhering the side of the channel substrate i10 in which the solvent bath i12 is formed to the cover substrate i11.

The sample cell i3' is disposed such that the surface of the reflection mirror substrate i7c in which the concave mirror i9 is formed (example of a reflective surface) is positioned downstream of the solvent bath i12 (example of a sample container section) in the incident direction of the excitation light E. Accordingly, the concave mirror i9 reflects the excitation light E that passes through the solvent bath i12 (sample container section) such that the excitation light is incident on the solvent bath i12 (sample container section) again.

It is not necessary that the reflection mirror substrate i7c have the concave mirror i9, and a normal plane mirror may also be used. In addition, in the case in which the sample spreads over a large area in the solvent bath and is to be evenly irradiated with the excitation light, the reflective surface may also be convex or planar. The concave portion of the concave mirror i9 may be filled with the same material as the material of the channel substrate i11. Alternatively, the concave portion may also be hollow.

FIG. 16 shows a sample cell i3″ according to another embodiment of the present invention. The sample cell i3″ includes a reflection mirror substrate i7c that is integrated with the sample cell i3″ and a cover member i11′ having a lens portion i14 that functions as a light-collecting optical system. The cover member i11′ is disposed on the incident side of a solvent bath i12 (sample container section) on which the excitation light is incident. According to this structure, the sample cell i3″ itself serves as an optical system that collects the excitation light E before it is incident on the sample.

In the above-described embodiments, the reflection mirrors i7a to i7c reflect the excitation light E only once to redirect the excitation light E toward the sample. However, the present invention is not limited to this, and the structure in which the redirected excitation light that passes through the sample is reflected toward the sample again (excitation light is repeatedly reflected) is also included in the technical scope of the present invention.

Eighth Embodiment

A photothermal conversion measurement apparatus jX1 according to an eighth embodiment of the present invention will be described below with reference to FIG. 19.

As shown in FIG. 19, the photothermal conversion measurement apparatus jX1 includes an FT interference excitation light source j101, mirrors j102 to j104, a concave mirror j105, a filter unit j106, a mirror j107, a measurement interference optical system j108, and an FT calculation signal processor j109.

A sample cell j5 containing a liquid sample is placed at a position where excitation light E is collected by the concave mirror j105 in the photothermal conversion measurement apparatus jX1. In photothermal conversion measurement apparatuses jX1 to jX4 according to eighth to eleventh embodiments, which will described below, the sample cell j5 includes a container member for containing the sample and a solvent (example of an enclosing agent) filling the container member excluding the sample itself.

The structures of the eighth to eleventh embodiments may be applied in combination with the structures of the first to fourth embodiments.

The FT interference excitation light source j101 emits the excitation light E. The excitation light E is reflected by the mirrors j102 to j104 and passes through the filter unit j106. The present embodiment is characterized by the filter unit j106, which will be described in detail below. The mirrors j102 to j104 are driven by the FT interference excitation light source j101. More specifically, the FT interference excitation light source j101 switches between the state in which the excitation light E is guided to the sample cell j5 and the state in which the excitation light E is not guided to the sample cell j5 at a predetermined period. The excitation light E is collected by the concave mirror j105 and is incident on the sample cell j5.

The sample cell j5 is also irradiated with the measurement light M (polarized wave M1) emitted from the measurement interference optical system j108. The measurement interference optical system j108 includes components corresponding to the measurement light source j6, the half-wave plate j7, the beam splitter j8, the acousto-optical modulators j9 and j10, the mirrors j11 and j12, the PBSs j13 and j14, the mirror j15, the quarter-wave plates j16 and j18, the photodetector j17, the reflection mirror j19, and the polarizing plate j20 shown in FIG. 17. The measurement light M (polarized wave M1) is reflected by the mirror j107, passes through the sample cell j5 again, and is detected by the measurement interference optical system j108.

As described above with reference to FIG. 17, the property change of the sample in the sample cell j5 caused by heat generated by the sample when the sample is irradiated with the excitation light E is detected by the measurement interference optical system j108 on the basis of the interference light of the measurement light (polarized wave M1) and the reference light. Then, an interference-light intensity signal having an output level corresponding to the obtained detection result is input to the FT calculation signal processor j109 from the measurement interference optical system j108. In addition, a mirror drive information signal representing the drive information of the mirror j102 is also input to the FT calculation signal processor j109 from the FT interference excitation light source j101.

The FT calculation signal processor j109 performs a signal process (FT calculation process) of the interference-light intensity signal and the mirror drive information signal to obtain data representing the wavelength of the excitation light.

If the wavelength range of the excitation light E includes an absorption wavelength range of the container member or the solvent included in the sample cell j5, a part of the excitation light E is absorbed by the container member or the solvent and the container member or the solvent generates heat. The generated heat causes a background signal in the interference-light intensity signal and reduces the analysis accuracy of the sample. Accordingly, the photothermal conversion measurement apparatus jX1 includes the filter unit j106 that eliminates components of the absorption wavelength ranges of the container member and the solvent.

Filter Unit Included in Photothermal Conversion Measurement Apparatus

FIG. 20 is a schematic diagram illustrating a characteristic portion of the photothermal conversion measurement apparatus jX1. As shown in FIG. 20, in the photothermal conversion measurement apparatus jX1, the filter unit j106 is disposed on an optical path along which the excitation light E emitted from the FT interference excitation light source j101 travels toward the sample cell j105. The filter unit j106 will be described in detail below. In FIGS. 20 to 23, the mirrors j102 to j105 are not shown for simplicity.

The filter unit j106 includes a filter j110a and two lenses j111a and j111b. The filter j110a reduces or eliminates components with the main absorption wavelength ranges of the container member (sample cell member) and the solvent (example of enclosing agent) included the sample cell j5 from the excitation light E incident on the sample cell j5. A wavelength-selecting filter, such as a bandpass filter and a sharp cut filter, is used as the filter j110a.

Here, the case in which the frequency ranges (frequency is a reciprocal of wavelength) of light absorbed by the sample, the container member, and the solvent are as those shown in the graphs of FIGS. 18A, 18B, and 18C, respectively, will be considered. In this case, the filter j110a eliminates a frequency component of 1100 $cm^{-1}$ and frequency components in the range of 1470 $cm^{-1}$ to 1550 $cm^{-1}$ from the excitation light E. Accordingly, members other than the sample, that is, the container member, the solvent, etc., are prevented from absorbing the excitation light E and generating heat. As a result, the analysis accuracy of the sample is increased.

The lenses j111a and j111b are provided to increase the diameter of the excitation light E when the excitation light E passes through the filter j110a. The density of the excitation light E is reduced by the lenses j111a and j111b when the excitation light E passes through the filter j110a, and accordingly the efficiency of eliminating the components with the above-described absorption wavelength ranges using the filter j110a is increased.

Ninth Embodiment

If the excitation light E includes components with the absorption wavelength ranges of the sample and the sample cell but a component with the absorption wavelength range of the solvent contained in the sample cell is small, the structure may also be such that only the component with the absorption wavelength range of the sample cell is eliminated from the excitation light E.

According to a ninth embodiment of the present invention, which will be described below, a photothermal conversion measurement apparatus jX2 includes a filter that eliminates the component with the absorption wavelength range of the sample cell.

FIG. 21 is a schematic diagram illustrating a characteristic portion of the photothermal conversion measurement apparatus jX2. The photothermal conversion measurement apparatus jX2 will be described below with reference to FIG. 21.

As shown in FIG. 21, the photothermal conversion measurement apparatus jX2 includes a filter j110b that is composed of a sample cell member made of the same material as the material of a container member included in the sample cell j5. When the excitation light E passes through the filter j110b composed of the sample cell member, a component with the absorption wavelength range of the sample cell member is eliminated from the excitation light E. Accordingly, the container member in the sample cell j5 is prevented from generating heat.

The filter j110b composed of the sample cell member preferably has a sufficient thickness (dimension in the incident direction of the excitation light E) so that the component with the absorption wavelength range of the sample cell member is reliably eliminated.

It is not necessary that the filter j110b be made of exactly the same material as the material of the sample cell member. More specifically, the filter j110b may also include a member similar to the sample cell that has an absorption wavelength range similar to that of the sample cell member (main absorption wavelength range of the container member (sample cell member)). In such a case, it is necessary to select a material whose absorption wavelength range does not include the absorption wavelength range of the sample as the material similar to the sample cell member.

Tenth Embodiment

If the excitation light E includes a component with the absorption wavelength range of the sample and a component with the absorption wavelength range of only the solvent (example of an enclosing agent) enclosed in the sample cell together with the sample, the structure may also be such that only the component with the absorption wavelength range of the solvent is eliminated.

According to a tenth embodiment of the present invention, which will be described below, a photothermal conversion measurement apparatus jX3 includes a filter including a solvent container (example of an enclosing-agent container) that contains the solvent.

FIG. 22 is a schematic diagram illustrating a characteristic portion of the photothermal conversion measurement apparatus jX3. The photothermal conversion measurement apparatus jX3 will be described below with reference to FIG. 22.

As shown in FIG. 22, the photothermal conversion measurement apparatus jX3 includes a filter j110c including a solvent container (example of an enclosing-agent container) that contains a solvent identical to that enclosed in a sample cell j5. When the excitation light E passes through the filter j110c, a component with the absorption wavelength range of the solvent is eliminated from the excitation light E. Accordingly, the solvent in the sample cell j5 is prevented from generating heat.

If the excitation light E includes components with the absorption wavelength ranges of the solvent (example of an enclosing agent) and the container member in addition to the component with the absorption wavelength range of the sample, the solvent container (example of an enclosing-agent container) may be formed of the same material as the material of the container member of the sample cell.

Eleventh Embodiment

FIG. 23 is a schematic diagram illustrating a characteristic portion of a photothermal conversion measurement apparatus jX4 according to an eleventh embodiment of the present invention.

As shown in FIG. 23, a filter j110b described in the ninth embodiment (filter composed of a sample cell member) and a filter j110c in which the solvent is enclosed may be arranged in series along the optical path of the excitation light E.

With regard to the industrial applicability of the present invention, the present invention is applicable to photothermal conversion measurement.

What is claimed is:

1. A photothermal conversion measurement apparatus for measuring a property change of a sample caused by a photothermal effect of the sample when the sample is irradiated with excitation light, the photothermal conversion measurement apparatus comprising:

measurement-light-emitting means for irradiating the sample with predetermined measurement light;

measurement-position-changing means for changing a measurement position at which a traveling path of the measurement light passes through an excitation section in the sample, the excitation section being excited by the excitation light; and light-measuring means for measuring the property change of the sample at each measurement position set by the measurement-position-changing means on a basis of the measurement light after the measurement light passes through the sample, wherein a phase change of the measurement light that passes through the sample is measured as the property change of the sample, wherein the measurement-position-changing means includes optical-path-changing means that changes the measurement position by changing an optical path of the excitation light, and wherein the optical-path-changing means includes first optical-path-changing means that changes an incident position and/or an incident direction of the excitation light that is incident on the sample in a direction that intersects an incident direction of the measurement light on the sample.

2. The photothermal conversion measurement apparatus according to claim 1, wherein the optical-path-changing means includes:

a lens that allows the excitation light to pass therethrough in substantially the same direction as an incident direction of the measurement light on the sample while collecting the excitation light; and second optical-path-changing means that moves the lens in substantially the same direction as the incident direction of the measurement light to change a focus position of the excitation light in the sample.

3. The photothermal conversion measurement apparatus according to claim 1, wherein the measurement-position-changing means includes sample-moving means that changes the measurement position by moving the sample.

4. The photothermal conversion measurement apparatus according to claim 1, further comprising:

two light-reflecting means arranged so as to face each other across the sample and repeatedly reflecting the measurement light incident on the sample between the two light-reflecting means along one axis while allowing the measurement light to pass through the sample, at least one of the two light-reflecting means allowing a part of the measurement light to pass therethrough; and light-intensity-detecting means that receives the measurement light that passes through said at least one of the light-reflecting means in a direction away from the sample and detects an intensity of the received measurement light.

5. The photothermal conversion measurement apparatus according to claim 4, further comprising a distance-adjusting means for adjusting a distance between the two light-reflecting means such that variation in a signal detected by the light-intensity-detecting means is reduced.

6. The photothermal conversion measurement apparatus according to claim 4, further comprising:

intensity-modulating means for periodically modulating the intensity of the excitation light incident on the sample; and periodic-component-extracting means that extracts a periodic component with the same period as a intensity modulation period of the excitation light from the signal detected by the light-intensity-detecting means.

7. The photothermal conversion measurement apparatus according to claim 4, further comprising variable spectroscopic means that outputs light obtained by dividing white light into spectral components as the excitation light and varies the wavelength range of the excitation light.

8. The photothermal conversion measurement apparatus according to claim 1, further comprising excitation-light-deflecting means that deflects the excitation light after the excitation light passes through the sample so that the excitation light is redirected to the sample.

9. The photothermal conversion measurement apparatus according to claim 8, wherein the excitation-light-deflecting means redirects the excitation light such that the excitation light is incident on the sample at the same portion as a portion at which the excitation light is incident on the sample the first time.

10. The photothermal conversion measurement apparatus according to claim 1, further comprising light-collecting means that collects the excitation light at a predetermined portion in the sample.

11. The photothermal conversion measurement apparatus according to claim 10, wherein the light-collecting means includes a lens and/or a concave mirror.

12. The photothermal conversion measurement apparatus according to claim 11, wherein the photothermal conversion measurement apparatus includes a single concave mirror that serves as both the excitation-light-deflecting means and the light-collecting means that collects the excitation light that passes through the sample.

13. The photothermal conversion measurement apparatus according to claim 1, further comprising filter means for reducing or eliminating a component with a main light-absorption wavelength range of a sample cell in which the sample is contained from the excitation light incident on the sample.

14. The photothermal conversion measurement apparatus according to claim 13, wherein the filter means includes a wavelength selecting filter.

15. The photothermal conversion measurement apparatus according to claim 13, wherein the filter means includes a member similar to the sample cell, the member being made of a material having the main light-absorption wavelength range of the sample cell.

16. The photothermal conversion measurement apparatus according to claim 13, wherein the filter means includes a sample cell member that is made of the same material as the material of the sample cell.

17. The photothermal conversion measurement apparatus according to claim 16, wherein the sample cell member functions as the enclosing-agent container.

18. The photothermal conversion measurement apparatus according to claim 13, wherein the filter means includes an enclosing-agent container containing an enclosing agent identical to that enclosed in the sample cell together with the sample.

19. A photothermal conversion measurement apparatus for measuring a property change of a sample caused by a photothermal effect of the sample when the sample is irradiated with excitation light, the photothermal conversion measurement apparatus comprising:

measurement-light-emitting means for irradiating the sample with predetermined measurement light;

measurement-position-changing means for changing a measurement position at which a traveling path of the measurement light passes through an excitation section in the sample, the excitation section being excited by the excitation light; and light-measuring means for measuring the property change of the sample at each measurement position set by the measurement-position-changing means on a basis of the measurement light after the measurement light passes through the sample, wherein a phase change of the measurement light that passes through the sample is measured as the property change of the sample, wherein the measurement-position-changing means includes optical-path-changing means that changes the measurement position by changing an optical path of the excitation light, and wherein the optical-path-changing means includes:

a lens that allows the excitation light to pass therethrough in substantially the same direction as an incident direction of the measurement light on the sample while collecting the excitation light; and second optical-path-changing means that moves the lens in substantially the same direction as the incident direction of the measurement light to change a focus position of the excitation light in the sample.

* * * * *